(12) United States Patent
Myers et al.

(10) Patent No.: US 10,433,873 B2
(45) Date of Patent: *Oct. 8, 2019

(54) EXTERNAL FIXATION

(71) Applicant: Zimmer, Inc., Warsaw, IN (US)

(72) Inventors: Thomas Myers, Marietta, GA (US); Robert V. O'Toole, Lutherville, MD (US); Jason W. Nascone, Highland, MD (US); Douglas M. Lorang, San Jose, CA (US); Andrew Fauth, River Heights, UT (US); Daniel J. Triplett, Providence, UT (US)

(73) Assignee: Zimmer, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/995,538

(22) Filed: Jun. 1, 2018

(65) Prior Publication Data

US 2018/0271561 A1  Sep. 27, 2018

Related U.S. Application Data

(62) Division of application No. 15/073,264, filed on Mar. 17, 2016, now Pat. No. 10,010,348, which is a
(Continued)

(51) Int. Cl.
*A61B 17/64* (2006.01)

(52) U.S. Cl.
CPC ...... *A61B 17/6458* (2013.01); *A61B 17/6416* (2013.01); *A61B 17/6425* (2013.01)

(58) Field of Classification Search
CPC ............ A61B 17/6491; A61B 17/6483; A61B 17/6475; A61B 17/6466; A61B 17/6458; A61B 17/64; A61B 17/66
See application file for complete search history.

(56) References Cited

U.S. PATENT DOCUMENTS

| 2,238,870 A | 4/1941 | Haynes |
| 2,393,831 A | 1/1946 | Stader |

(Continued)

FOREIGN PATENT DOCUMENTS

| CN | 1169279 A | 1/1998 |
| CN | 1494397 A | 5/2004 |

(Continued)

OTHER PUBLICATIONS

US 6,030,385 A, 02/2000, Faccioli et al. (withdrawn)
(Continued)

*Primary Examiner* — Julianna N Harvey
(74) *Attorney, Agent, or Firm* — Schwegman Lundberg & Woessner, P.A.

(57) ABSTRACT

External fixation systems, and methods for immobilizing joints or fractured bones. An external fixation system may include one or more clamp assemblies connected to one or more rod assemblies at polyaxial joints. Each rod assembly may be length adjustable, and may include a one-way locking mechanism to provisionally lock the length of the rod assembly, and additional locking mechanisms to permanently lock the length of the rod assembly. The system may be deployed pre-assembled as a unit to immobilize a joint or fracture. Another external fixation system further includes a spanning member extending transverse to the rod assemblies. Two or more external fixation systems may be deployed in a stacked configuration on one set of bone pins to immobilize two joints and/or fractures. The systems may be provided in kits including guiding instrumentation, bone pins and pin clamping assemblies for connecting the bone pins to the external fixation systems.

20 Claims, 27 Drawing Sheets

Related U.S. Application Data division of application No. 13/961,729, filed on Aug. 7, 2013, now Pat. No. 9,301,782.

(60) Provisional application No. 61/696,695, filed on Sep. 4, 2012, provisional application No. 61/775,239, filed on Mar. 8, 2013.

(56) References Cited

U.S. PATENT DOCUMENTS

| | | |
|---|---|---|
| 4,135,505 A | 1/1979 | Day |
| 4,273,116 A | 6/1981 | Chiquet |
| 4,600,000 A | 7/1986 | Edwards et al. |
| 4,717,076 A | 1/1988 | Notkin |
| 4,745,913 A | 5/1988 | Castaman et al. |
| 5,207,676 A | 5/1993 | Canadell et al. |
| 5,275,599 A | 1/1994 | Zbikowski et al. |
| 5,314,426 A | 5/1994 | Pohl et al. |
| 5,356,421 A | 10/1994 | Castro |
| 5,376,090 A | 12/1994 | Pennig |
| 5,380,322 A | 1/1995 | Van Den Brink et al. |
| 5,403,313 A | 4/1995 | Lin |
| 5,439,465 A | 8/1995 | Tumibay |
| 5,443,464 A | 8/1995 | Russell et al. |
| 5,451,226 A | 9/1995 | Pfeil et al. |
| 5,454,810 A | 10/1995 | Pohl et al. |
| 5,591,164 A | 1/1997 | Nazre et al. |
| 5,658,283 A | 8/1997 | Huebner |
| 5,660,363 A | 8/1997 | Maglica |
| 5,672,175 A | 9/1997 | Martin |
| 5,688,271 A | 11/1997 | Faccioli et al. |
| 5,702,389 A | 12/1997 | Taylor et al. |
| 5,738,684 A | 4/1998 | Thomas et al. |
| 5,741,252 A | 4/1998 | Mazzio et al. |
| 5,766,173 A | 6/1998 | Ross, Jr. et al. |
| 5,769,851 A | 6/1998 | Veith |
| 5,891,144 A | 4/1999 | Mata et al. |
| 5,921,985 A | 7/1999 | Ross, Jr. et al. |
| 5,941,877 A | 8/1999 | Viegas et al. |
| 5,951,556 A | 9/1999 | Faccioli et al. |
| 5,961,515 A | 10/1999 | Taylor et al. |
| 5,976,136 A | 11/1999 | Bailey et al. |
| 6,010,501 A | 1/2000 | Raskin et al. |
| 6,080,153 A | 6/2000 | Mata et al. |
| 6,102,911 A | 8/2000 | Faccioli et al. |
| 6,162,224 A | 12/2000 | Huebner et al. |
| 6,171,308 B1 | 1/2001 | Bailey et al. |
| 6,176,860 B1 | 1/2001 | Howard |
| 6,176,881 B1 | 1/2001 | Schar et al. |
| 6,203,548 B1 | 3/2001 | Helland |
| 6,221,072 B1 | 4/2001 | Termaten |
| 6,235,029 B1 | 5/2001 | Faccioli et al. |
| 6,245,071 B1 | 6/2001 | Pierson |
| 6,277,118 B1 | 8/2001 | Grant et al. |
| 6,328,737 B1 | 12/2001 | Moorcroft et al. |
| 6,409,729 B1 | 6/2002 | Martinelli et al. |
| 6,428,540 B1 | 8/2002 | Claes et al. |
| 6,482,206 B2 | 11/2002 | Schoenefeld |
| 6,500,177 B1 | 12/2002 | Martinelli et al. |
| 6,520,961 B1 | 2/2003 | Marsh |
| 6,530,925 B2 | 3/2003 | Boudard et al. |
| 6,569,164 B1 | 5/2003 | Assaker et al. |
| 6,578,801 B2 | 6/2003 | Attee |
| 6,613,049 B2 | 9/2003 | Winquist et al. |
| 6,652,523 B1 | 11/2003 | Evrard et al. |
| 6,702,814 B2 | 3/2004 | Walulik et al. |
| 6,793,655 B2 | 9/2004 | Orsak |
| 6,840,939 B2 | 1/2005 | Venturini et al. |
| 6,860,883 B2 | 3/2005 | Janowski et al. |
| 6,913,587 B2 | 7/2005 | Slishman et al. |
| 6,988,696 B2 | 1/2006 | Attee et al. |
| 7,048,735 B2 | 5/2006 | Ferrante et al. |
| 7,147,639 B2 | 12/2006 | Berki et al. |
| 7,241,074 B2 | 7/2007 | Thomke et al. |
| 7,261,713 B2 | 8/2007 | Langmaid et al. |
| 7,282,052 B2 | 10/2007 | Mullaney |
| 7,306,601 B2 | 12/2007 | Mcgrath et al. |
| 7,311,711 B2 | 12/2007 | Cole |
| 7,320,555 B2 | 1/2008 | Chang et al. |
| 7,749,224 B2 | 7/2010 | Cresina et al. |
| 7,875,030 B2 | 1/2011 | Hoffmann-Clair |
| 7,931,650 B2 | 4/2011 | Winquist et al. |
| 8,029,546 B2 | 10/2011 | Capote |
| 8,057,474 B2 | 11/2011 | Knuchel et al. |
| 8,147,490 B2 | 4/2012 | Bauer |
| 8,157,295 B2 | 4/2012 | Krywitsky |
| 8,206,418 B2 | 6/2012 | Triplett et al. |
| 8,262,656 B2 | 9/2012 | Mirza et al. |
| 8,303,587 B2 | 11/2012 | Lehmann et al. |
| 8,323,281 B2 | 12/2012 | Hotchkiss et al. |
| 8,343,166 B2 | 1/2013 | Maughan et al. |
| 8,425,512 B2 | 4/2013 | Vasta et al. |
| 8,672,978 B2 | 3/2014 | Dant et al. |
| 8,734,446 B2 | 5/2014 | Miller |
| 9,301,782 B2 | 4/2016 | Myers et al. |
| 9,918,748 B2 | 3/2018 | Kalfas et al. |
| 9,924,969 B2 | 3/2018 | Triplett |
| 9,962,187 B2 | 5/2018 | Erickson |
| 10,010,348 B2 | 7/2018 | Myers et al. |
| 2004/0059331 A1 | 3/2004 | Mullaney |
| 2004/0133199 A1 | 7/2004 | Coati et al. |
| 2005/0131409 A1 | 6/2005 | Chervitz et al. |
| 2006/0155276 A1 | 7/2006 | Walulik et al. |
| 2006/0229602 A1 | 10/2006 | Olsen et al. |
| 2006/0287652 A1 | 12/2006 | Lessig et al. |
| 2007/0086849 A1 | 4/2007 | Chang et al. |
| 2007/0123856 A1 | 5/2007 | Deffenbaugh et al. |
| 2009/0036892 A1 | 2/2009 | Karidis et al. |
| 2009/0118733 A1 | 5/2009 | Orsak et al. |
| 2009/0228006 A1 | 9/2009 | Mussolin |
| 2009/0299368 A1* | 12/2009 | Bauer .................. A61B 17/645 606/57 |
| 2009/0306499 A1 | 12/2009 | Van Vorhis et al. |
| 2010/0249779 A1 | 9/2010 | Hotchkiss et al. |
| 2010/0312243 A1 | 12/2010 | Ross et al. |
| 2010/0331840 A1 | 12/2010 | Ross et al. |
| 2011/0098707 A1 | 4/2011 | Mullaney |
| 2011/0172665 A1 | 7/2011 | Winquist et al. |
| 2011/0245830 A1 | 10/2011 | Zgonis et al. |
| 2012/0150186 A1 | 6/2012 | Hajianpour |
| 2012/0253410 A1 | 10/2012 | Taylor et al. |
| 2012/0303029 A1 | 11/2012 | Vasta et al. |
| 2012/0303032 A1 | 11/2012 | Mirza et al. |
| 2013/0110110 A1 | 5/2013 | Waisman |
| 2013/0274807 A1 | 10/2013 | Prajapati |
| 2013/0296857 A1* | 11/2013 | Barnett .............. A61B 17/6416 606/57 |
| 2014/0066931 A1 | 3/2014 | Myers et al. |
| 2014/0088649 A1 | 3/2014 | Refai |
| 2014/0316468 A1 | 10/2014 | Keiser et al. |
| 2014/0350558 A1 | 11/2014 | Triplett et al. |
| 2015/0100089 A1 | 4/2015 | Richelsoph et al. |
| 2015/0282842 A1 | 10/2015 | Beyar et al. |
| 2015/0337890 A1 | 11/2015 | Faccioli et al. |
| 2016/0038184 A1 | 2/2016 | Erickson |
| 2016/0199099 A1 | 7/2016 | Myers et al. |
| 2016/0367291 A1 | 12/2016 | Erickson et al. |
| 2018/0098792 A1 | 4/2018 | Triplett et al. |
| 2018/0161066 A1 | 6/2018 | Erickson |

FOREIGN PATENT DOCUMENTS

| | | |
|---|---|---|
| CN | 101184447 A | 5/2008 |
| CN | 102368981 A | 3/2012 |
| CN | 10461927 A | 5/2015 |
| CN | 104619276 B | 8/2016 |
| CN | 106794034 A | 5/2017 |
| CN | 107645936 A | 1/2018 |
| EP | 0639352 A1 | 2/1995 |
| EP | 0807419 A2 | 11/1997 |
| EP | 1238636 A1 | 9/2002 |
| FR | 2520607 A3 | 8/1983 |
| JP | 2004350774 A | 12/2004 |
| JP | 2017523864 A | 8/2017 |

(56) References Cited

FOREIGN PATENT DOCUMENTS

| JP | 2018509247 A | 4/2018 |
|---|---|---|
| WO | WO-9427514 A1 | 12/1994 |
| WO | WO-9516401 A1 | 6/1995 |
| WO | WO-2006126167 A2 | 11/2006 |
| WO | WO-2012122317 A2 | 9/2012 |
| WO | WO-2014039205 A1 | 3/2014 |
| WO | WO-2016025375 A1 | 2/2016 |
| WO | WO-2016154107 A1 | 9/2016 |
| WO | WO-2016205128 A1 | 12/2016 |
| WO | WO-2016205128 A2 | 12/2016 |
| WO | WO-2016205128 A3 | 12/2016 |

OTHER PUBLICATIONS

"U.S. Appl. No. 13/961,729, Final Office Action dated Sep. 30, 2015", 13 pgs.
"U.S. Appl. No. 13/961,729, Non Final Office Action dated May 15, 2015", 13 pgs.
"U.S. Appl. No. 13/961,729, Notice of Allowance dated Nov. 24, 2015", 5 pgs.
"U.S. Appl. No. 13/961,729, Response filed Apr. 24, 2015 to Restriction Requirement dated Mar. 19, 2015", 6 pgs.
"U.S. Appl. No. 13/961,729, Response filed Jul. 1, 2015 to Non Final Office Action dated May 15, 2015", 12 pgs.
"U.S. Appl. No. 13/961,729, Response filed Nov. 4, 2015 to Final Office Aciton dated Sep. 30, 2015", 10 pgs.
"U.S. Appl. No. 13/961,729, Restriction Requirement dated Mar. 19, 2015", 8 pgs.
"U.S. Appl. No. 14/456,407, Advisory Action dated Feb. 9, 2017", 3 pgs.
"U.S. Appl. No. 14/456,407, Final Office Action dated Oct. 28, 2016", 11 pgs.
"U.S. Appl. No. 14/456,407, Non Final Office Action dated Apr. 28, 2016", 10 pgs.
"U.S. Appl. No. 14/456,407, Non Final Office Action dated Jun. 13, 2017", 11 pgs.
"U.S. Appl. No. 14/456,407, Notice of Allowance dated Sep. 29, 2017", 8 pgs.
"U.S. Appl. No. 14/456,407, Notice of Allowance dated Nov. 8, 2017", 9 pgs.
"U.S. Appl. No. 14/456,407, Response Filed Jan. 27, 2017 to Final Office Action dated Oct. 28, 2016", 9 pgs.
"U.S. Appl. No. 14/456,407, Response filed Apr. 11, 2016 to Restriction Requirement dated Feb. 19, 2016", 9 pgs.
"U.S. Appl. No. 14/456,407, Response filed Jul. 28, 2016 to Non Final Office Action dated Apr. 28, 2016", 9 pgs.
"U.S. Appl. No. 14/456,407, Response filed Aug. 30, 2017 to Non Final Office Action dated Jun. 13, 2017", 8 pgs.
"U.S. Appl. No. 14/456,407, Restriction Requirement dated Feb. 19, 2016", 7 pgs.
"U.S. Appl. No. 14/668,282, Final Office Action dated Jun. 1, 2017", 21 pgs.
"U.S. Appl. No. 14/668,282, Non Final Office Action dated Nov. 15, 2016", 16 pgs.
"U.S. Appl. No. 14/668,282, Notice of Allowance dated Aug. 16, 2017", 8 pgs.
"U.S. Appl. No. 14/668,282, Notice of Allowance dated Dec. 18, 2017", 7 pgs.
"U.S. Appl. No. 14/668,282, Preliminary Amendment filed May 5, 2015", 3 pgs.
"U.S. Appl. No. 14/668,282, Response filed Feb. 15, 2017 to Non Final Office Action dated Nov. 15, 2016", 11 pgs.
"U.S. Appl. No. 14/668,282, Response filed Jul. 26, 2017 to Final Office Action dated Jun. 1, 2017", 8 pgs.
"U.S. Appl. No. 14/668,282, Response filed Oct. 31, 2016 to Restriction Requirement dated Sep. 15, 2016", 9 pgs.
"U.S. Appl. No. 14/668,282, Restriction Requirement dated Sep. 15, 2016", 8 pgs.
"U.S. Appl. No. 15/073,264, Amendment Under 37 C.F.R. § 1.312", 7 pgs.
"U.S. Appl. No. 15/073,264, Non Final Office Action dated Oct. 2, 2017", 13 pgs.
"U.S. Appl. No. 15/073,264, Notice of Allowance dated Feb. 27, 2018", 9 pgs.
"U.S. Appl. No. 15/073,264, Preliminary Amendment filed Mar. 17, 2016", 3 pgs.
"U.S. Appl. No. 15/073,264, Response filed Jul. 14, 2017 to Restriction Requirement dated Jan. 14, 2017", 7 pgs.
"U.S. Appl. No. 15/073,264, Response filed Dec. 19, 2017 to Non Final Office Action dated Oct. 2, 2017", 10 pgs.
"U.S. Appl. No. 15/073,264, Restriction Requirement dated Jun. 14, 2017", 6 pgs.
"U.S. Appl. No. 15/180,946, Restriction Requirement dated Dec. 13, 2017", 8 pgs.
"U.S. Appl. No. 15/839,459, Preliminary Amendment filed Dec. 13, 2017", 42 pgs.
"Application Serial No. PCT/US2016/023400, Invitation to Pay Additional Fees and Partial Search Report dated May 27, 2016", 7 pgs.
"Chinese Application Serial No. 201380046175.X, Office Action dated Oct. 29, 2015", (W/ English Translation), 8 pgs.
"Chinese Application Serial No. 201380046175.X, Response filed Feb. 24, 2016 to Office Action dated Oct. 29, 2015", (W/ English Translation), 8 pgs.
"European Application Serial No. 15751264.1, Response filed Oct. 9, 2017 to Office Action dated Mar. 28, 2017", 14 pgs.
"International Application Serial No. PCT/US2013/054058, International Preliminary Report on Patentability dated Mar. 19, 2015", 7 pgs.
"International Application Serial No. PCT/US2013/054058, International Search Report dated Oct. 14, 2013", 4 pgs.
"International Application Serial No. PCT/US2015/044441, International Preliminary Report on Patentability dated Feb. 23, 2017", 12 pgs.
"International Application Serial No. PCT/US2015/044441, International Search Report dated Jan. 25, 2016", 6 pgs.
"International Application Serial No. PCT/US2015/044441, Invitation to Pay Additional Fees and Partial Search Report dated Oct. 22, 2015", 5 pgs.
"International Application Serial No. PCT/US2015/044441, Written Opinion dated Jan. 25, 2016", 10 pgs.
"International Application Serial No. PCT/US2016/023400, International Preliminary Report on Patentability dated Oct. 5, 2017", 10 pgs.
"International Application Serial No. PCT/US2016/023400, International Search Report dated Aug. 9, 2016", 6 pgs.
"International Application Serial No. PCT/US2016/023400, Written Opinion dated Aug. 9, 2016", 8 pgs.
"International Application Serial No. PCT/US2016/037228, International Search Report dated Feb. 14, 2017", 7 pgs.
"International Application Serial No. PCT/US2016/037228, Written Opinion dated Feb. 14, 2017", 6 pgs.
Stryker, "Hoffman II MRI, External Fixation Systems Brochure", Literature No. 5075-1-600, LotD4508, Copyright 2008, 12 pgs.
Stryker, "Hoffmanxpress Brochure", Literature No. 982336, Lot B0409, Copyright 2009, 24 pgs.
"U.S. Appl. No. 14/456,407, Corrected Notice of Allowance dated Feb. 27, 2018", 4 pgs.
"U.S. Appl. No. 14/668,282, Corrected Notice of Allowance dated Mar. 30, 2018", 2 pgs.
"U.S. Appl. No. 15/073,264, PTO Response to Rule 312 Communication dated Jun. 5, 2018", 2 pgs.
"U.S. Appl. No. 15/180,946, Non Final Office Action dated Apr. 17, 2018", 12 pgs.
"U.S. Appl. No. 15/180,946, Response filed Jan. 11, 2018 to Restriction Requirement dated Dec. 13, 2017", 9 pgs.
"U.S. Appl. No. 15/180,946, Response filed Jun. 8, 2018 to Non Final Office Action dated Apr. 17, 2018", 13 pgs.
"U.S. Appl. No. 15/839,459, Supplemental Preliminary Amendment filed Dec. 19, 2017", 6 pgs.

(56) References Cited

OTHER PUBLICATIONS

"U.S. Appl. No. 15/892,704, Preliminary Amendment filed Feb. 13, 2018", 6 pgs.
"International Application Serial No. PCT/US2016/037228, International Preliminary Report on Patentability dated Dec. 28, 2017", 8 pgs.
"U.S. Appl. No. 15/180,946, Non Final Office Action dated Nov. 21, 2018", 15 pgs.
"Chinese Application Serial No. 201580053427.0, Office Action dated Nov. 5, 2018", (W/ English Translation), 12 pgs.
"European Application Serial No. 16713258.8, Response filed Aug. 30, 2018 to Office Action dated Jul. 25, 2018", 12 pgs.
"European Application Serial No. 16732138.9, Response filed Jul. 19, 2018 to Office Action dated Feb. 16, 2018", 14 pgs.

\* cited by examiner

EXTERNAL FIXATION

CROSS-REFERENCE TO RELATED APPLICATIONS

This application is a non-provisional of:

U.S. Provisional Patent Application No. 61/696,695, filed Sep. 4, 2012, and is entitled EXTERNAL FIXATOR; and U.S. Provisional Patent Application No. 61/775,239, filed Mar. 8, 2013, and is entitled EXTERNAL FIXATOR.

The above-identified documents are incorporated herein by reference.

FIELD OF THE DISCLOSURE

This disclosure relates to systems, devices and methods for external fixation. More specifically, this disclosure relates to systems for providing external fixation to joints and/or fractured bones.

BACKGROUND OF THE INVENTION

The present disclosure relates to systems, devices and methods for long bone external fixation. Bone external fixation is useful in several applications, for example, for use in short-term stabilization of traumatic injuries, long-term stabilization of traumatic injuries, short- or long-term stabilization of a joint, and limb-lengthening stabilization during the healing process.

The systems, devices and methods described herein may be used for stabilization of a traumatic injury until a long-term stabilization device can be applied. Short-term or temporary stabilization may allow soft tissues to recover from trauma prior to definitive skeletal fixation; for example reduction of swelling, healing of open wounds, and/or healing of skin abrasions prior to open reduction and internal fixation. External fixation may also be used when transportation is required from the site of initial care, such as a local or rural hospital to a secondary site with appropriate trauma capabilities, such as a regional trauma center. Short-term stabilization may also be used for injuries that occur during periods of time when appropriate trauma care is not available, such as after hours, until a skilled clinician becomes available. Short-term stabilization may be appropriate in battlefield or field hospital situations. There is a need for external fixation systems and methods which are simple, easy, and affordable.

In fixation systems known in the art, significant time may be spent assembling clamp bodies on the back table. In many cases, the same components are used each time. During implantation over the fracture or joint, sliding rods, moving clamps and other numerous parts requiring individual adjustment make the application and tightening of the frame cumbersome. There is a need for a frame that requires no pre-assembly and can simply be placed over the fracture or joint, have the first set of pins placed on one side of the joint, stretch the frame over the joint and place the second set of pins as desired on the second side of the joint. There would be no assembly and no possibility of rods sliding out of the clamps in such an arrangement.

In many situations, before an external fixation frame can be locked down, the fracture/joint must be restored to its proper length. In order to do this, the limb must be stretched against the natural tension in the muscles. This force is significant, as some surgeons report that they pull until "their feet begin to slide on the floor". In systems known in the art, the surgeon must hold this tension as an assistant tightens all the clamps in the frame. There is a need for a one-way motion lock that holds the limb length once it has been established. This would allow the surgeon to make minor adjustments as necessary and lock the frame in a less technically demanding manner and potentially without as much assistance from other scrubbed personnel as is needed with systems known in the art.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
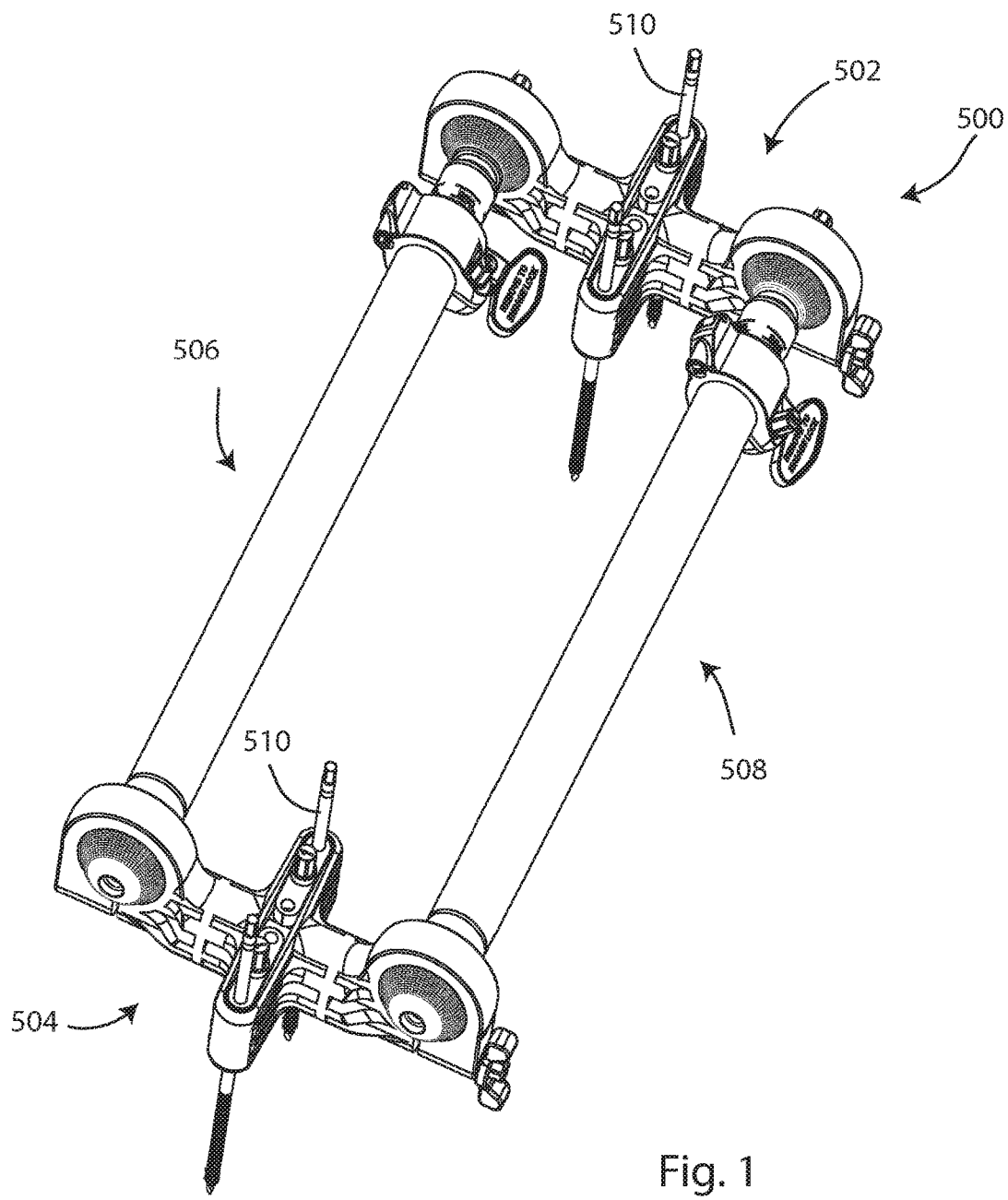
FIG. 1 is a perspective view of an external fixation system including a first clamping assembly, a second clamping assembly, and two rod assemblies captured in the first and second clamping assemblies, the external fixation system mounted on a plurality of bone pins.

The present disclosure relates to external fixation systems and methods for their use. Those of skill in the art will recognize that the following description is merely illustrative of the principles of the technology, which may be applied in various ways to provide many different alternative embodiments. This description is made for the purpose of illustrating the general principles of this technology and is not meant to limit the inventive concepts in the appended claims. While the present disclosure is made in the context of knee or ankle joint or fracture fixation for the purposes of illustrating the concepts of the design, it is contemplated that the present design and/or variations thereof may be suited to applications in the arm, wrist, finger, toe, spine, or other bones or joints.

The technology described herein may relate to an external fixation clamp that utilizes at least one polyaxial joint to provide for a highly adaptable connection between a bone and a stiffening rod.

The devices, kits and methods of the present disclosure can provide an external fixation system which is economically disposable. The systems of the present disclosure may be manufactured at such a low cost that they can be considered disposable after one use. For example, a kit of the present disclosure may be made for a manufacturer's suggested retail price (MSRP) of about $500. Each of the external fixation systems disclosed herein may be provided pre-assembled in a kit which may also include tools and/or fixation members such as pins. In a method of use, bone pins may be fixed in bone portions of a patient, to span a fracture and/or an anatomical joint. The pre-assembled external fixation system is mounted on the bone pins as a single piece or unit, and provisionally locked by pulling one end of the system away from the opposite end, thus setting the fracture and/or immobilizing the anatomic joint. After the provisional locking, which holds the joint or fracture immobilized, individual connections and clamps of the system may be adjusted and further locked down. The external fixation system may remain on the patient for a short term period of time which may include transportation time. For example, a complex ankle fracture such as a pylon (pilon) fracture might be initially treated with an external fixator until swelling lessens one or two weeks later and it is safer to make skin incisions to treat the fracture definitively. The patient might be transported to another hospital or rehabilitation facility between the time of initial external fixator placement and definitive surgery. In another example, one or more systems of the present disclosure may be used on a patient in a battlefield or at an accident site, and left in the locked down configuration on the patient through transportation to a hospital, where surgery or other long-term means are used to stabilize the fracture or joint.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk.

In this specification, a standard system of three mutually perpendicular reference planes is employed. A sagittal plane divides a body into bilaterally symmetric right and left portions. A coronal plane divides a body into anterior and posterior portions. A transverse plane divides a body into superior and inferior portions.

In an aspect of a method for external fixation of a limb, the limb having a first bone portion and a second bone portion, the method includes: securing a first bone pin to the first bone portion; securing a second bone pin to the second bone portion; attaching a pre-assembled external fixation system to the first bone pin, the external fixation system including: first and second clamp assemblies, first rod assemblies, and a one-way locking mechanism; the first rod assembly joined to each of the first and second clamp assemblies, the first and second clamp assemblies at opposite longitudinal ends of the first rod assemblies; the first clamp assembly received over the first bone pin; attaching the external fixation system to the second bone pin, the second clamp assembly received over the second bone pin; applying tension to distract the first clamp assembly longitudinally away from the second clamp assembly to increase a length of the external fixation system between the first clamp assembly and the second clamp assembly; and releasing the tension on the first clamp assembly, wherein when the tension on the first clamp assembly is released the one-way locking mechanism automatically engages to prevent the length of the external fixation system from decreasing.

In an embodiment, the method may include: opening a package; and removing the pre-assembled external fixation system as a single unit from the package In another embodiment, each rod assembly includes a removable tab, the method including: removing the tab to activate the one-way locking mechanism, wherein prior to removal of the tab, the external fixation system is freely adjustable to increase or decrease the length of the external fixation system between the first clamp assembly and the second clamp assembly;

In yet another embodiment, the external fixation system includes a second rod assembly, the second rod assembly joined to each of the first and second clamp assemblies.

In yet another embodiment, the first clamp assembly is identical to the second clamp assembly, and the first rod assembly is identical to the second rod assembly.

In yet another embodiment, the one-way locking mechanism automatically engages the rod assembly to prevent the length of the external fixation system from decreasing.

In yet another embodiment, the one-way locking mechanism automatically engages the rod assembly at a non-discrete location to prevent the length of the external fixation system from decreasing.

In yet another embodiment, the rod assembly includes an inner tubular member received in an outer tubular member, wherein the one-way locking mechanism is a first locking mechanism, wherein the one-way locking mechanism is mounted to the outer tubular member, wherein activating the one-way locking mechanism further includes: directly engaging the one-way locking mechanism with the inner tubular member to prevent the inner tubular member from translating relative to the outer tubular member in a first direction.

In yet another embodiment, the one-way locking mechanism includes a collar encircling the inner tubular member, wherein the collar frictionally engages with the inner tubular member to prevent the inner tubular member from translating relative to the outer tubular member in the first direction.

In yet another embodiment, the method includes: activating a second locking mechanism to further prevent the inner tubular member from translating relative to the outer tubular member in the first direction and also in a second direction opposite the first direction.

In yet another embodiment, the rod assembly further includes the second locking mechanism, the second locking mechanism including a clamp encircling the outer tubular member, the method further including: compressing the clamp around the outer tubular member; and compressing the outer tubular member around the inner tubular member.

In yet another embodiment, the method includes: activating a third locking mechanism to further prevent the inner tubular member from translating relative to the outer tubular member.

In yet another embodiment, the rod assembly further includes the third locking mechanisms, the third locking mechanism including a plug received in the inner tubular member, the method further including drawing the plug within the inner tubular member to expand a portion of the inner tubular member.

In yet another embodiment, the method includes: polyaxially adjusting the position of the first rod assembly relative to the first clamp assembly; and compressing the first clamp assembly about the first rod assembly to lock the position of the first rod assembly relative to the first clamping assembly.

In yet another embodiment, the method includes: locking the first clamping assembly to the first bone pin.

In yet another embodiment, the first clamping assembly houses a first fixation plate and a second fixation plate, wherein locking the first clamping assembly to the first bone pin further includes: passing the first bone pin through the first and second fixation plates; and deforming the first and second fixation plates to bind against the first bone pin.

In yet another embodiment, the method includes: passing a third bone pin into the first clamping assembly; and securing the third bone pin to the limb.

In an aspect of an external fixation system, the system includes: a first clamp assembly; a second clamp assembly; a first rod assembly secured to and extending between the first clamp assembly and the second clamp assembly, the first rod assembly including a first tubular member and a second tubular member received in the first tubular member; and a one-way locking mechanism which limits axial translation between the first tubular member and the second tubular member, the one-way locking mechanism having an unlocked configuration and a locked configuration; wherein the external fixation system has a length measured between the first clamp assembly and the second clamp assembly; wherein when the one-way locking mechanism is in the unlocked configuration the second tubular member can freely translate relative to the first tubular member to increase or decrease the length of the external fixation system; and wherein when the one-way locking mechanism is in the locked configuration second tubular member can freely translate relative to the first tubular member to increase the combined length of the external fixation system but is prevented from translating relative to the first tubular member to decrease the length of the external fixation system.

In an embodiment, the external fixation system includes a second rod assembly secured to and extending between the first clamp assembly and the second clamp assembly, wherein the first clamp assembly is identical to the second clamp assembly, and wherein the first rod assembly is identical to the second rod assembly.

In another embodiment, the second tubular member can axially translate in a first direction to increase the length of the external fixation system and in a second direction opposite the first direction to decrease the length of the external fixation system.

In yet another embodiment, in the locked configuration the one-way locking mechanism engages the first rod assembly to prevent the length of the external fixation system from decreasing.

In yet another embodiment, the one-way locking mechanism further includes a collar encircling the second tubular member, wherein, in the locked configuration, the collar binds against the second tubular member to prevent translation of the second tubular member in the second direction.

In yet another embodiment, the one-way locking mechanism is a first locking mechanism, the system further including a second locking mechanism to further prevent the second tubular member from any motion relative to the first tubular member.

In yet another embodiment, the rod assembly further includes the second locking mechanism, the second locking mechanism including a clamp encircling the first tubular member, wherein the clamp is compressible about the first tubular member to compress the first tubular member around the second tubular member to prevent any motion relative to the first tubular member.

In yet another embodiment, the external fixation system includes a third locking mechanism which engages the first and second tubular members.

In yet another embodiment, the third locking mechanism includes a plug received in the second tubular member, wherein drawing the plug within the second tubular member expands a portion of the second tubular member to fit tightly within the first tubular member.

In yet another embodiment, the first clamp assembly includes a spherical clamping surface and the first rod assembly includes a spherical portion, the spherical portion received within the spherical clamping surface to form a polyaxial joint between the first clamp assembly and the first rod assembly.

In yet another embodiment, the first clamp assembly further includes a locking screw, wherein tightening the locking screw compresses the spherical clamping surface around the spherical portion to lock the position of the first rod assembly relative to the first clamping assembly.

In yet another embodiment, the external fixation system includes a second rod assembly including a second spherical portion, wherein the first clamping assembly further includes a second spherical clamping surface, the second spherical portion received within the second spherical clamping surface to form a polyaxial joint between the first clamp assembly and the second rod assembly, wherein tightening the locking screw simultaneously locks the positions of the first and second rod assemblies relative to the first clamping assembly.

In yet another embodiment, the external fixation system includes a first bone pin, wherein the first clamping assembly houses a first fixation plate and a second fixation plate, wherein the first bone pin passes through the first fixation plate and the second fixation plate, and the first and second fixation plates are deformable to bind against the first bone pin and fix the position of the first bone pin relative to the first clamping assembly.

In yet another embodiment, the external fixation system includes a removable tab attached to the one-way locking mechanism, wherein the removable tab holds the one-way locking mechanism in the unlocked configuration, wherein removal of the tab from the one-way locking mechanism converts the one-way locking mechanism to the locked configuration.

Figure 2:
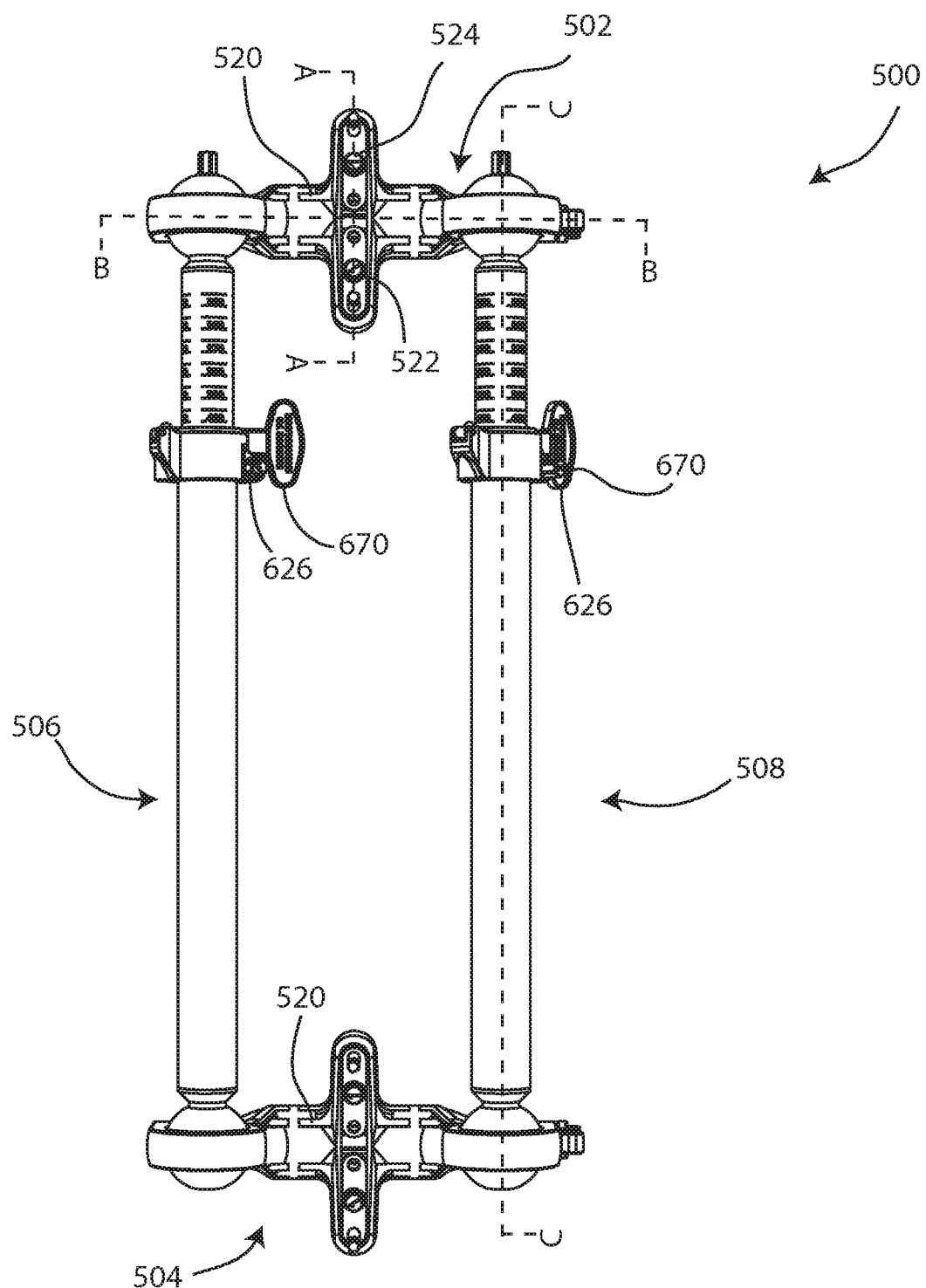
FIG. 2 is a top-down view of the external fixation system of FIG. 1.

Referring to FIGS. 1 and 2, an external fixation system 500 includes a first clamping assembly 502, a second clamping assembly 504, a first rod assembly 506 and a second rod assembly 508. In an embodiment, external fixation system 500 may be referred to as a knee spanning system or joint spanning system, although external fixation system 500 may also be used to span a fracture, osteotomy, epiphyseal plate, or other discontinuity between bone portions. The rod assemblies 506, 608 extend between and connect the clamping assemblies 502, 504 into the single system 500. The rod assemblies 506, 508 may be scaled to an appropriate size for the knee or other anatomical site. In some embodiments, the second rod assembly 508 may be omitted. The connections between the rod assemblies and clamping assemblies are polyaxially adjustable. The clamping assemblies may be referred to as support elements or members, as they support the rod assemblies. The rod assemblies may be referred to as variable length or telescoping elements, struts, or members, as the length of each is adjustable. The external fixation system 500 may be referred to as a frame. The first and second clamping assemblies may be mirror images, or may be identical to one another, as may the first and second rod assemblies. Using identical assemblies in a system may enable the entire system to be produced more cheaply and/or quickly than a system in which each separate component or assembly is unique. For example the system 500 with identical assemblies 502, 504 and 506, 508 may require fewer forms and unique production processes than a system having multiple unique and non-identical components. Assembly may also be faster as there may be fewer steps, and certain assembly steps may be repeated.

In use, system 500 can be secured to the patient in one piece, as a unit. First clamping assembly 502 may be fixed to a first bone portion by one or more fixation pins 510. Bone screws, bone pins, wires, and/or other fasteners may be used in place of or in combination with fixation pins 510. Second clamping assembly 504 may be fixed to a second bone portion by additional fixation pin(s) 510. The rod assemblies 506 and 508, extending between the clamping assemblies, may span a joint or fracture between the first and second bone portions. After the clamping assemblies 502, 504 are fixed to the bone portions, the rod assemblies 506, 508 may be lengthened or shortened to a desired length and provisionally locked to stabilize the joint or fracture. Following the provisional locking, the polyaxial connections of the assembly may be adjusted, then more permanently locked.

Referring to FIGS. 3-6, clamping assembly 502 is shown in more detail. Clamping assembly 504 may be a mirror image, or may be identical to clamping assembly 502 and will not be described in further detail; the description of clamping assembly 502 also applies to clamping assembly 504. Clamping assembly 502 includes a clamp body 520 which is formed as a single piece. Clamping assembly 502 further includes first and second fixation bolts 522, 524; first, second, third and fourth fixation plates 526, 527, 528 and 529; a clamping bolt 530; first nut 532; and second nut 533. The fixation plates may be referred to as locking plates. The rod assemblies 506, 508 are polyaxially adjustably connected to the clamping assembly 502 via a first clamp 534 and a second clamp 536 which are formed as part of the clamping body 520. In some embodiments, the second clamp 536 may be omitted. Two bone pins 560, 562 extend through the clamping body 520 to fix the clamping assembly 502 to a bone portion. In another embodiment, only one bone pin may be used.

Figure 4:
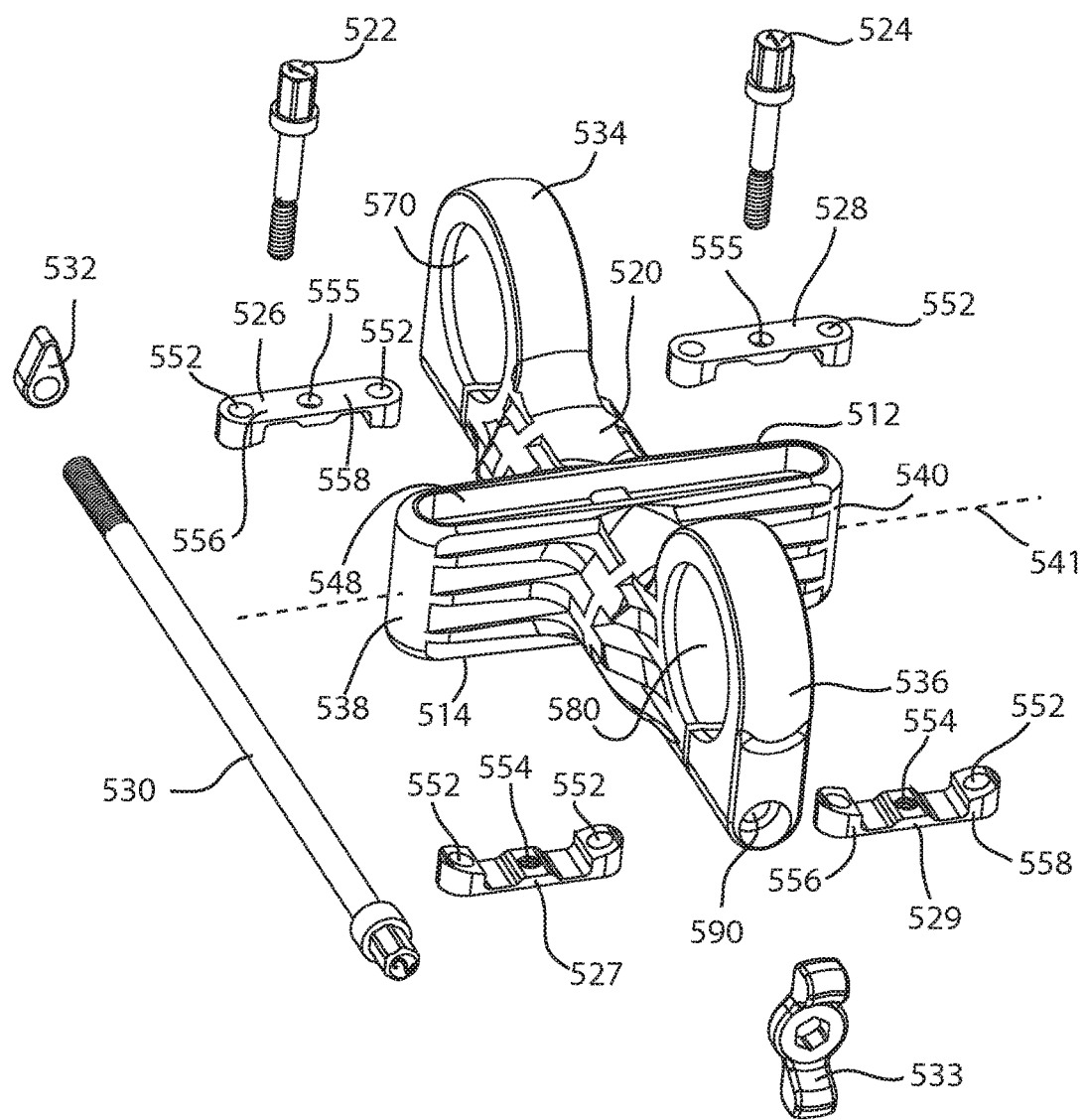
FIG. 4 is an exploded view of a clamping assembly of FIG. 1.
Figure 5:
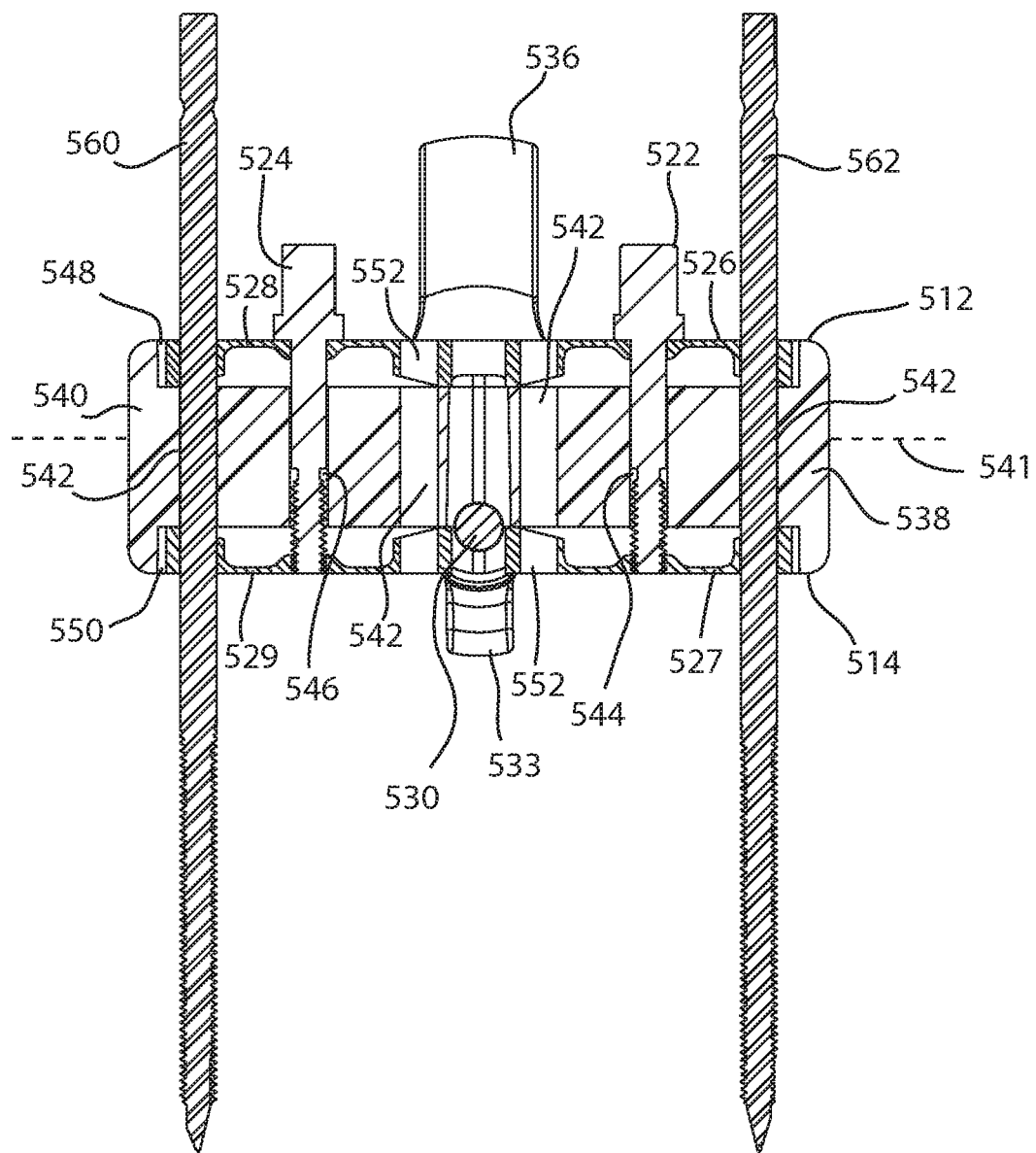
FIG. 5 is a cross-sectional view of the clamping assembly of FIG. 1 taken along line A-A of FIG. 2.

Referring to FIGS. 2, 4 and 5, clamp body 520 may be cruciform or plus-shaped and includes an upper or first surface 512 and a lower or second surface 514 opposite the first surface. The clamp body 520 further includes a first arm 538 and a second arm 540 which extend along a first axis 541, perpendicular to the first and second clamps 534, 536 which extend along a second axis 535. First axis 541 may be parallel to the longitudinal lengths of rod assemblies 506, 508 when the system 500 is in a neutral or orthogonal arrangement. Two bolt openings 544, 546 extend through the clamping body 520 in the same direction as the pin openings 542, 552 described below. In the example shown, the bolt and pin openings extend in a direction perpendicular to the first axis 541 and the second axis 535. A first slot 548 is recessed into the first surface 512, and a second slot 550 is recessed into the second surface 514, opposite the first slot. The first and second slots are elongated, occupying the majority of the length of the first and second arms 538, 540, and slots are parallel with first axis 541. A plurality of pin openings or bores 542 extend through the arms between the first and second slots 548, 550, each pin bore sized to receive a bone pin 510. First and second fixation plates 526, 528 are housed in the first slot 548, and third and fourth fixation plates are housed in the second slot 550. Each fixation plate 526, 527, 528 and 529 includes at least one plate pin opening 552, and one of a threaded plate bolt opening 554 or a non-threaded plate bolt opening 555. Each fixation plate 526, 527, 528 and 529 is elongated, having a first extension 556 and a second extension 558.

The bone pins 560, 562 are received in pin openings 542 of clamp body 520. As seen in FIGS. 4 and 5, each bone pin may pass through a plate pin opening 552 in a fixation plate, through the first slot 548, through a pin bore 542, through the second slot 550, and out through a plate pin opening 552 in another fixation plate. The opening for the pins may be non-threaded and/or smooth, to allow the pins 560, 562 to initially be axially translatable relative to the arms 538, 540. The translation allows for adjustability of the height of the system 500 relative to a patient's limb, which may be advantageous if there are tissue swelling, open wounds, and/or skin abrasions on the limb. It is appreciated that the bone pins may be placed in one or any combination of the pin openings 542.

Referring to FIG. 5, the first fixation bolt 522 passes through a non-threaded bolt opening 554 in first fixation plate 526, into the slot 548, through a bolt opening 544 and out through second slot 550 and a threaded plate bolt opening 555 in second fixation plate 527. As the threads of bolt 522 engage threaded plate bolt opening 555, the second fixation plate 527 is drawn toward the first fixation plate 526, and one or both of fixation plates 527, 526 may be elastically or plastically deformed. The plate pin openings 552 frictionally bind against pin 562, preventing it from further axial translation. As the plates 526, 528 deform they may bow and decrease in length, which pushes the pin 562 against the side wall of the pin bore 542. This force creates a secondary locking action relative to the pin 562. The bolt 524 passes through bolt opening 554 in third fixation plate 528, through a bolt opening 544 and out through second slot 550 and a threaded plate bolt opening 555 in fourth fixation plate 529. Bolt 524 engages with plates 528, 529 in the same manner as described for bolt 522 to fix pin 560. It is appreciated that in other embodiments, other methods of pin capture or fixation known in the art may be used.

Figure 6:
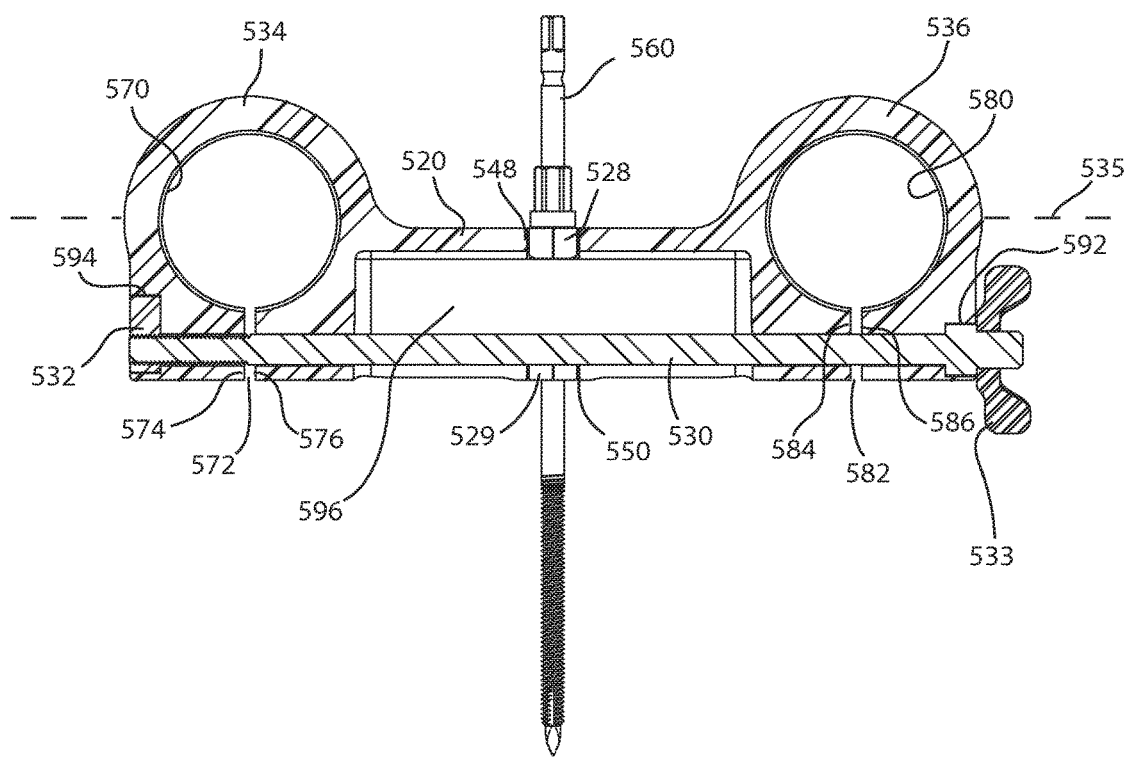
FIG. 6 is a cross-sectional view of the clamping assembly of FIG. 1 taken along line B-B of FIG. 2.
Figure 7:
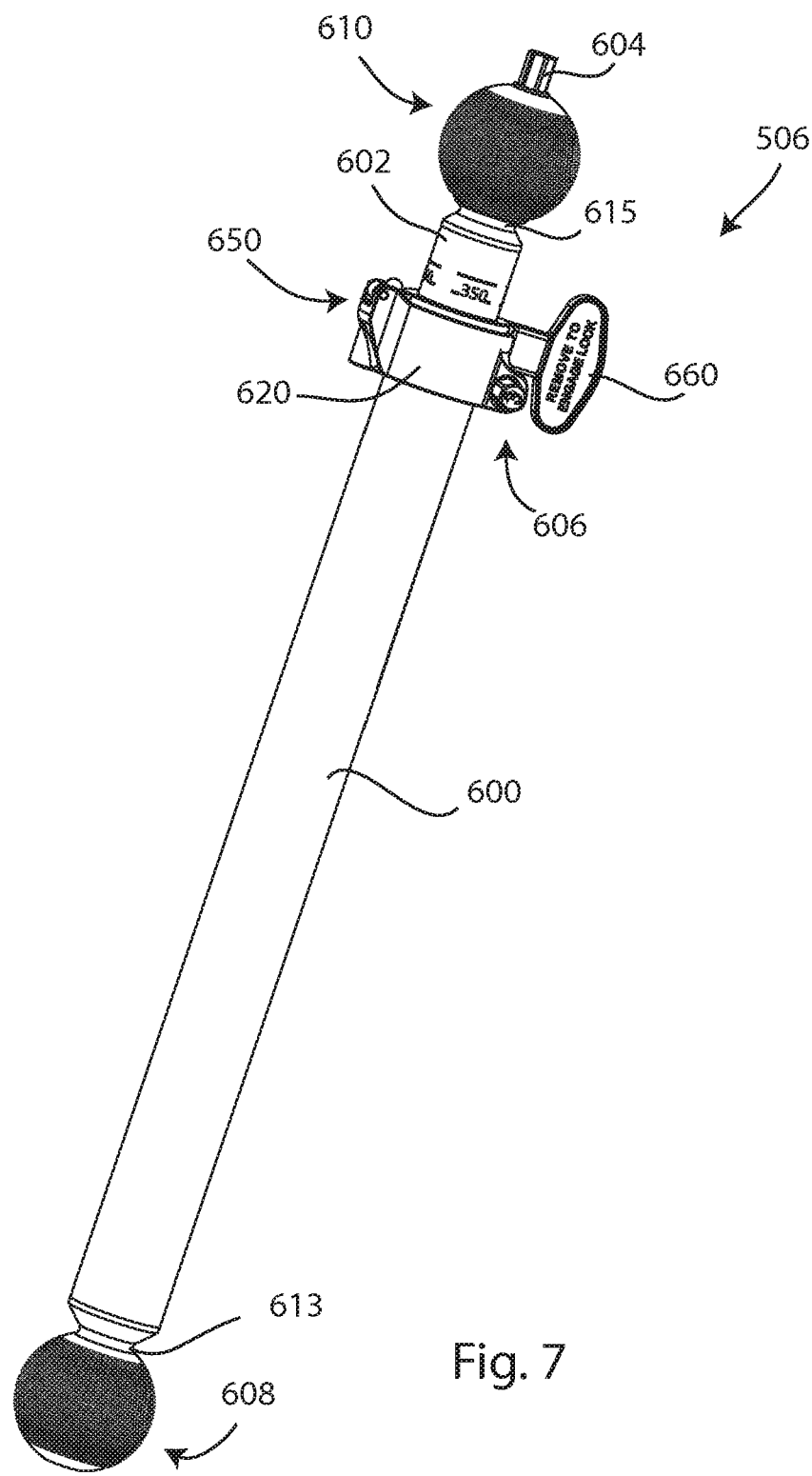
FIG. 7 is a perspective view of a rod assembly of FIG. 1.
Figure 8:
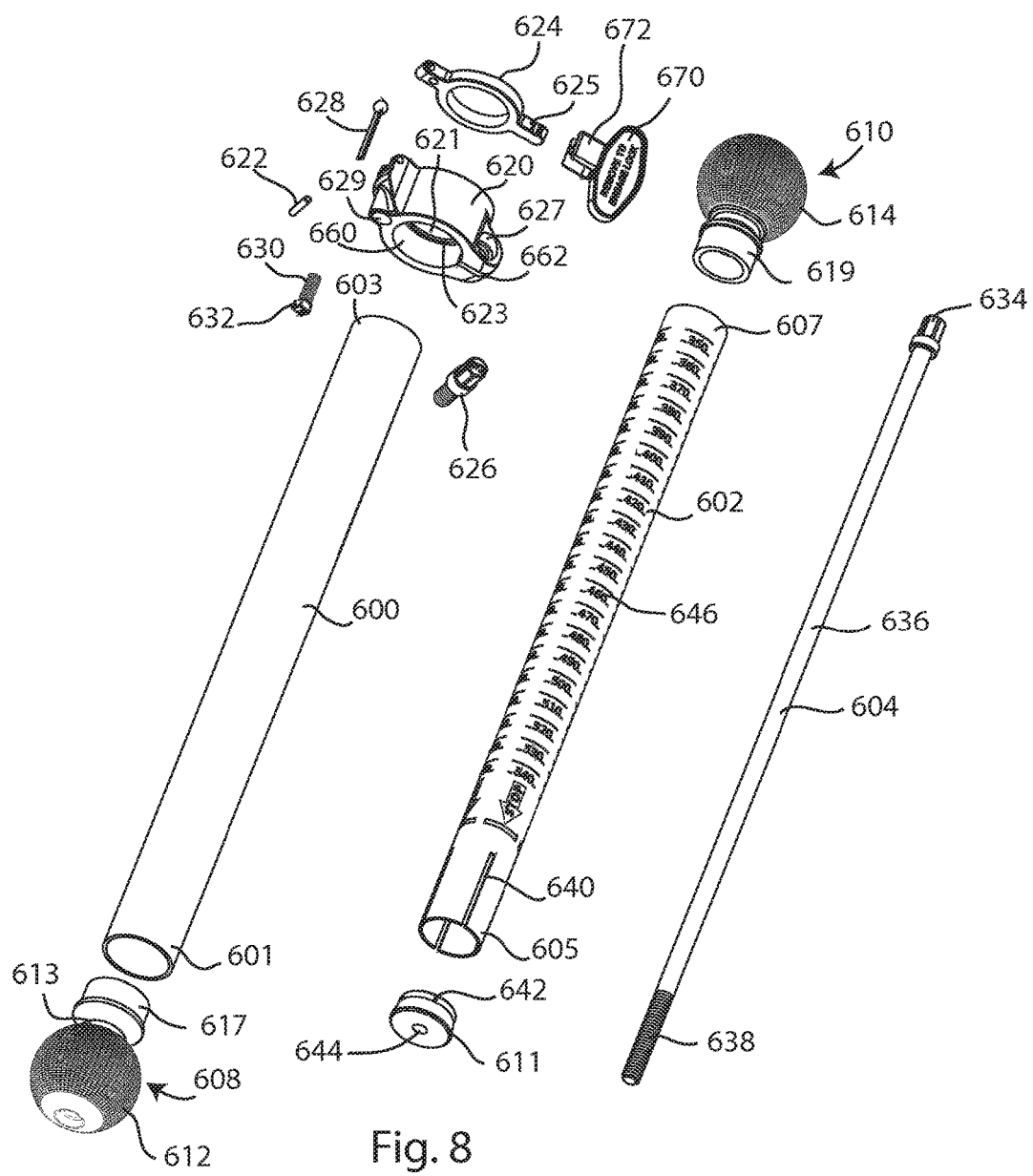
FIG. 8 is an exploded view of the rod assembly of FIG. 1.

Turning to FIGS. 4 and 6, clamps 534, 536 are shaped to retain or clamp rod assemblies 506, 508 while allowing telescoping movement of the rod assemblies to lengthen or shorten the rod assemblies. Clamp 534 has an inner clamping surface 570 which is spherical in the illustrated embodiment; in other embodiments the clamping surfaces may be partially spherical, conical, cylindrical, flat, polygonal, or another shape. In the embodiment shown, the clamps 534, 536 may be said to hold the corresponding spherical portions 612, 614 captive because the inner clamping surfaces 570, 580 are wide enough, parallel to axis 541, to cover an equatorial diameter, or great diameter, of the corresponding spherical portion 612, 614 sufficiently to interfere with disassembly at low loads. The inner clamping surface 570 is interrupted by a clamp gap 572 bounded by opposing first and second clamp surfaces 574, 576. Similarly, clamp 536 has a spherical inner clamping surface 580, clamp gap 582, and first and second clamping surfaces 584, 586. In the example shown the inner clamping surfaces 570, 580 are smooth but in an alternative embodiment they may be ridged or roughened. A bore 590 extends through clamps 534 and 536, parallel to second axis 535, intersecting clamp gaps 572, 582. Bore 590 also intersects with second slot 550 at the center of the clamp body 520. The bore 590 includes a first recess 592 at one end and a second recess 594 at the opposite end. A chamber 596 extends lengthwise within the clamp body 520 between the first clamp 534 and the second clamp 536, and may provide for weight reduction for the clamp body. Clamping bolt 530 extends through bore 590 and engages nut 532. As the clamping bolt 530 engages the nut 532, the nut 532 is captured in second recess 594. Further actuation of bolt 530 draws nut 532 toward the bolt head, engaging recess 594 and closing gaps 572, 582. Nut 533, which may be a wing nut, may also be actuated by hand to tighten bolt 530. As seen in FIG. 1, when rod assemblies 506, 508 are assembled with clamps 534, 536 as shown and bolt 530 is tightened as described, the rod assemblies are gripped in the clamps and prevented from any movement, for example axial, rotation, or polyaxial, relative to the clamp body 520. Nut 533 and bolt 530 may include coarse pitch threads for quick tightening.

Referring to FIGS. 7-10, rod assembly 506 is shown in more detail. Rod assembly 508 may be a mirror image, or may be identical to rod assembly 506 and will not be described further detail. Rod assembly 506 includes an outer or first tubular element 600, an inner or second tubular element 602, a locking screw 604 and a rod clamp assembly 606. The first tubular element 600 has a first end 601 and a second end 603 and shaft 609 extending therebetween; the second tubular element has a first end 605 and a second end 607 and a shaft 619 extending therebetween. The first tubular element 600 is larger in diameter than and coaxially receives a portion of the second tubular element 602. The tubular members may be circular in cross-section as shown, or in other embodiments may be square, rectangular, triangular, or any other polygonal shape in cross-section. The tubular elements may also be referred to as rods, rod elements, or rod members.

A first tube plug 608 is joined to the first end 601 of first tubular element 600 and a second tube plug 610 is joined to the second end 607 of second tubular element 602. An inner plug 611 fits inside the first end 605 of the inner tubular element 602. The tube plugs 608, 610 have convex spherical portions 612, 614 which are complementarily shaped to the concave spherical inner clamping surfaces 570, 580 of the clamps 534, 536. First tube plug 608 further includes a neck 613 and an attachment portion 617, and second tube plug 610 further includes a neck 615 and an attachment portion 619. The necks 613, 615 may be smaller in diameter than the respective spherical portions 612, 614, and the respective inner and outer tubular elements 600, 602. The attachment portions 617, 619 may be annular and hollow, and sized to be received in the respective tubular elements 600, 602. The large and small tube plugs 608, 610 may be made from machined aluminum. During manufacture they may be assembled to the associated tubes through insertion, bonding, gluing or threading, among other processes.

Figure 9:
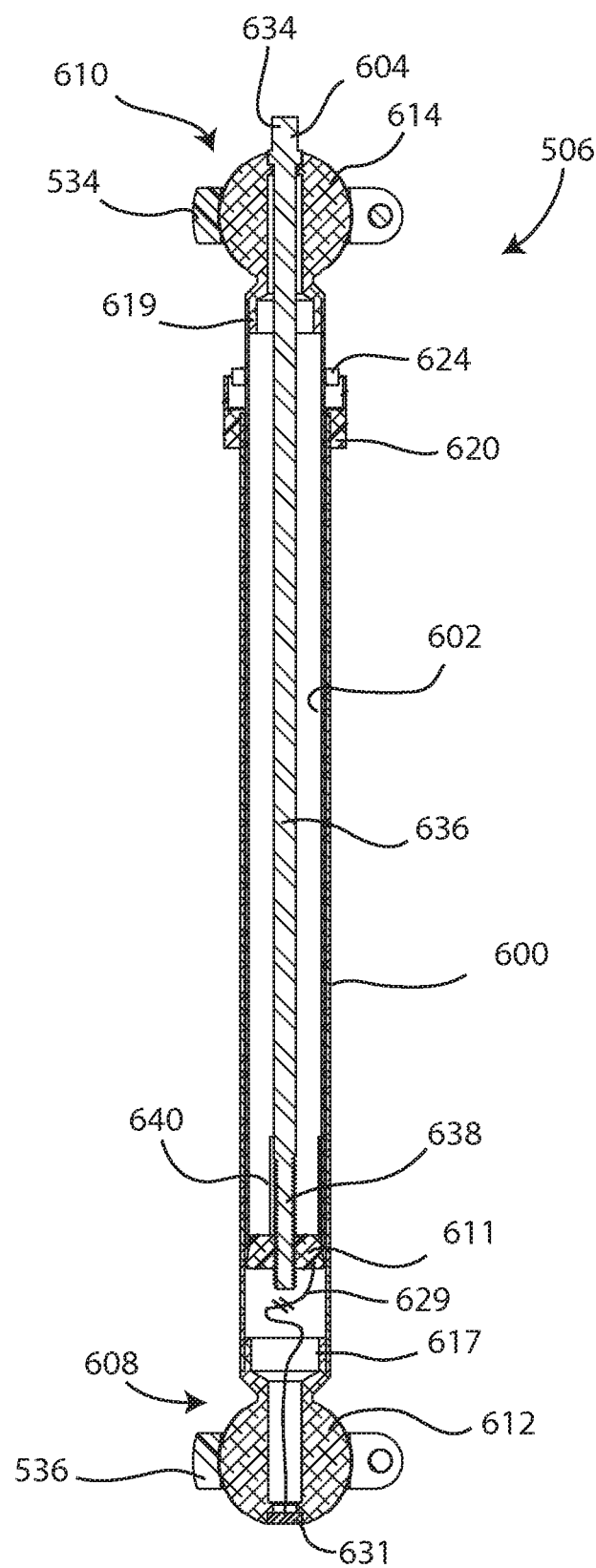
FIG. 9 is a longitudinal cross-sectional view of a rod assembly of FIG. 1 taken along line C-C of FIG. 2.

A line, chain, tether, or other connecting element may extend between inner plug 611 within second tubular element 602 and first tubular element 600, to prevent inadvertent disconnection between the tubular elements 600, 602. As seen in FIG. 9, a line 629 may be tethered to inner plug 611, extend through the bore of outer tubular element 600, and be tethered to a cap 631 received in tube plug 608. Line 629 may be of sufficient length to allow axial translation between the tubular elements; for example line 629 may be approximately the length of outer tubular element 600. In other embodiments, other retention features known in the art may be used to prevent disconnection between the first and second tubular elements.

The spherical portions 612, 614 of the plugs may feature an exterior pattern or texture to enhance the locking strength of the polyaxial clamps. A first pattern may be a negative feature, in which valleys, grooves or slots are cut into the outer surface of the sphere. This is effective where the clamp surface has sufficient compliance to deform elastically or plastically into the negative features. A second pattern may be a positive feature, such as spikes or sharp ridges that extend from the native, or nominal, spherical surface. These positive features are intended to press or cut into the clamp surface in order to create a mechanical interlock between the spherical portion and the clamp. The first pattern may enhance the clamping forces between the two elements without damaging either component. The second pattern may permanently deform one of the two elements, and may be less likely to be reversible. The embodiments disclosed herein may include the first or second patterns, a combination of the two, neither pattern, or another pattern. In other embodiments, texture may be provided by coatings or material deposits. The spherical portions may include openings that serve as drain holes, to permit fluid drainage when a patient bathes.

Figure 3:
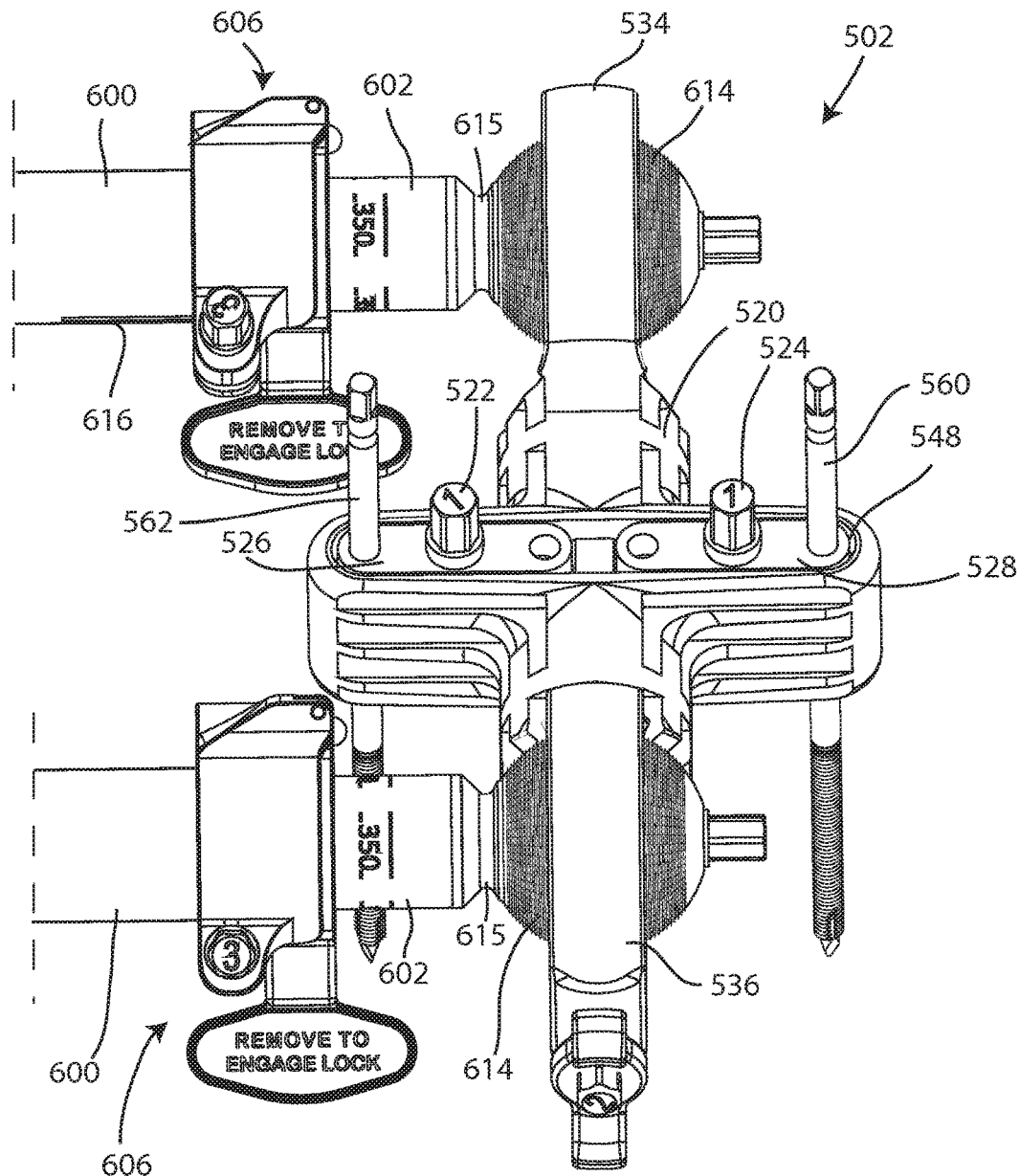
FIG. 3 is an enlarged perspective view of the first clamping assembly of FIG. 1, including two bone pins.

When assembled with the clamps 534, 536, as in FIGS. 1 and 3 for example, the spherical portions 612, 614 form polyaxially adjustable joints, allowing rotational motion about multiple axes. The polyaxial range of motion of the system 500 is a function of the thickness of the clamps 534, 536 parallel to axis 541, the diameter of the spherical portions 612, 614 of the tube plugs and the diameter of the necks 613, 615 that connect the spherical portion to the tubular element. The depicted embodiment features +/−30 degrees of motion at each polyaxially adjustable joint. In another embodiment, the range of motion may be +/−45 degrees at each polyaxially adjustable joint. If additional range of motion is required, this can be accomplished by reducing the thickness of the clamps, increasing the diameter of the spherical portions, and/or decreasing the diameter of the neck regions. As the diameter of the neck is reduced, the tube wall thickness may be thicker in order to maintain the same strength. An optimization exercise can be employed to determine the diameter and wall thickness that maximizes both the polyaxial range of motion and the component strength. It is appreciated that the locations of the spherical portions and clamping surfaces can also be reversed to achieve a polyaxial connection between the clamp assembly and a rod assembly. For example, in an embodiment the clamp body 520 may include a convex spherical portion and a rod assembly 506 or 508 may include a concave spherical clamping surface. In another embodiment, spherical portions 612, 614 may be split spheres which are expanded from within to lock with the spherical clamping surfaces 570, 580.

The spherical portions 612, 614 may have any size diameter according to the intended use of the external fixator embodiment. As the diameter of a spherical portion increases, the clamping force necessary to lock out motion between a spherical portion and its respective spherical clamping surface decreases, and can be reduced to a level that can be locked by finger tightening a wing nut, knob, lever, bolt, or the like. In an embodiment, the diameter of the spherical portion is 0.75 inches or larger. In another embodiment, the diameter of the spherical portion is 1.0 inch or larger. In another embodiment, the diameter of the spherical portion ranges from 1.25 to 1.75 inches. Embodiments with spherical portions of 0.75 inches or larger may be suited to use in the femur, knee, tibia, ankle, and/or foot.

It is appreciated that other embodiments contemplated within the scope of the disclosure include polyaxially adjustable joints at other locations on the systems disclosed herein. In another embodiment, polyaxially adjustable joints may be located at one or more locations along the length of the rod assemblies, instead of or in addition to the polyaxially adjustable joints at the ends of the rod assemblies, for example, they may be formed between first and second rod elements of the rod assemblies. In another embodiment, U-joints allowing rotational movement about two axes may be formed between the rod assemblies and the clamping assemblies. In another embodiment, polyaxially adjustable joints may be formed on the clamping assemblies instead of at the connections between the clamping assemblies and the rod assemblies. In another embodiment, polyaxially adjustable joints may be formed between the bone pins and the clamping bodies. Other embodiments may mix and match the joint locations disclosed herein.

The outer 600 and inner 602 tubes may be specified as standard sized, thin-walled aluminum tubing. They may also be manufactured from carbon fiber reinforced polymer or other materials that provide the desired stiffness and ability to associate with the tube plugs. The shafts 609, 619 may be smooth to facilitate sliding between them. Indicia 646 may be present on the outsides of the tubular elements to indicate the length of the rod assembly. In some embodiments, grooves may be present on the outside of tubular element 602 to catch binding collar 624 at discrete and/or predetermined positions. In some embodiments, a ratcheting connection may be formed between the first and second tubular elements.

In an embodiment, the rod clamp assembly 606 may be described as a split collar locking device. It may be bonded to the end of the outer tubular element 600 and is oriented to a short slot 616 in that tube. In the example shown in FIG. 8, the rod clamp assembly 606 includes a locking collar 620, a pin 622, a binding collar 624, a screw 626, a retention pin 628, a spring 630 and a retainer 632. The binding collar 624 is received in an annular recess 621 of the locking collar 620, and is hinged to the locking collar via pin 622. A tongue 625 protrudes from the binding collar 624. The retention pin 628 extends through a bore in the binding collar 624, through a pin bore 629 in the locking collar, through spring 630 and is captured by retainer 632. The locking collar 620 further includes a circular bore 660 which is interrupted by a collar gap 662. A first shoulder 664 and a second shoulder 666 are on opposite sides of the bore gap 662. Screw 626 is received in a screw bore 627 of the locking collar 620. The outer tubular element 600 is received in bore 660, with second end 603 seated against a flange 623.

Figure 10:
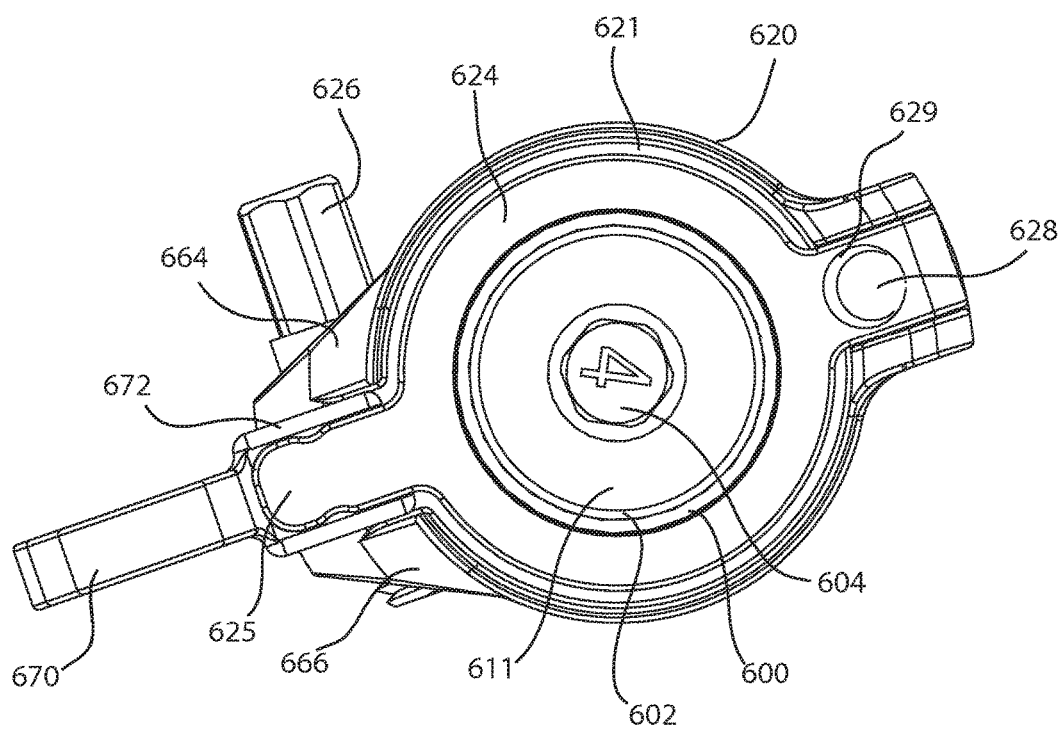
FIG. 10 is an end view of a rod assembly of FIG. 1, with a tube plug removed in order to show detail of a locking clamp.

The rod clamp assembly 606 further includes a tab member 670, which is removable to allow the rod clamp assembly 606 to be actuated to provisionally lock the first and second tube members 600, 602 in a fixed axial or length relationship. Tab member 670 includes a pair of tab extensions 672. As seen in FIG. 10, binding collar 624 is received in locking collar 620. In an unlocked configuration, tab member 670 is attached to the rod clamp assembly 606 with tab extensions 672 are on either side of tongue 625, captured between the tongue and the shoulders 664, 666. The presence of the tab member 670 keeps collar gap 662 open, allowing tubular members 600, 602 to axially move relative to one another in both directions, by preventing bore 660 from clamping around tubular members 600, 602 and provisionally locking the tubular members together. In use, tab member 670 may be present on the system 500 when it is removed from packaging, and allows telescoping adjustment of the length of system 500, in either axial direction, to shorten or lengthen the system 500.

A provisional, or temporary locking mechanism 650 allows the tubes 600, 602 to telescope outward, increasing in combined length, but prevents the tubes from collapsing, or decreasing in combined length, unless the lock is released. This type of locking may be described as a one-way motion lock. The rod assembly may be described as being length-stable when the temporary locking mechanism 650 is engaged. The provisional locking mechanism 650 allows for adjustment of the length of the rod assembly before the entire system 500 is locked down into a rigid configuration. This one-way locking mechanism has an unlocked configuration in which the second tubular member can freely translate relative the first tubular member to increase or decrease the length of the external fixation system, and a locked configuration in which the second tubular member can freely translate relative to the first tubular member to increase the combined length of the external fixation system but is prevented from translating relative to the first tubular member to decrease the length of the external fixation system. Removal of the tab member 670 converts the one-way locking mechanism from the unlocked to the locked configuration. Tab member 670 may be tethered to the system 500, for example via a line, lanyard, split ring, or the like, so that after tab member 670 is disengaged from the rod clamp assembly 606 the tab member 670 is not lost. The tab member 670 may be removed from the rod clamp assembly 606 and reinserted into the rod clamp assembly 606 repeatedly during a medical procedure.

The locking mechanism 650 includes the binding collar 624, locking collar 620, retention pin 628, spring 630 and retainer 632. After tab member 670 is removed, a closing force is applied by spring 630, the closing force pushing binding collar 624 against inner tubular element 602. In this state, tension may be applied to one or both tubular elements 600 and 602 to translate them coaxially apart to increase their combined length; for example, the second clamp assembly 504 may be distracted away from the first clamp assembly 502. As the elements are pulled apart binding collar 624 and retention pin 628 are advanced toward locking collar 620, freeing binding collar 624 from engagement with inner tubular element 602. Once the desired length of the rod assembly 506 is achieved, and the tension is released, the spring force causes binding collar 624 to bind against inner tube 602 provisionally locking the tubes 600, 602 together and preventing any decrease in their combined length. The closing force is required to ensure that the locking action is automatic and occurs without any backlash. In the context of this disclosure, automatic locking refers to locking that does not require any additional action by the user to accomplish the locking; once the pulling force ceases allowing binding collar 624 to bind against inner tube 602, the length of rod assembly 506 is locked without any further steps. It is appreciated that provisional locking mechanism 650 allows locking of the two tubular elements together anywhere along a continuum on the outer surface of inner tubular element 602. In other words, the provisional locking mechanism 650 allows locking of the two tubular elements together at any one of an infinite number of locations along the other surface of the inner tubular element. During system lengthening, binding collar 624 may be parallel with locking collar 620; during provisional locking, binding collar 624 may be angled relative to locking collar 620 as it binds against the inner tubular element.

After provisional locking, further locking of each rod assembly may be accomplished by turning screw 626. As screw 626 is tightened, the inner diameter of the locking collar 620 decreases and compresses over the rod slot 616, reducing the effective inside diameter of the large tube 600 until it compresses around the outside of the small tube 602. Screw 626 and plug 611 may include coarse pitch threads for quick tightening.

Locking screw 604 may also be tightened to more permanently fix the length of rod assembly 506, and/or to increase the rigidity of the rod assembly 506. The locking screw 604 and inner plug 611 act to remove any backlash or looseness that may exist between the outer diameter of the first end 605 of the small tube 602 and the inner diameter of the large tube 600. The locking screw 604 includes a screw head 634 and a shaft 636 with a threaded portion 638. The inner plug 611 includes a protrusion 642 and a threaded bore 644. As screw 604 is rotated, the threaded portion 638 of the screw engages the threaded bore 644 of the inner plug 611 and protrusion 642 indexes into one of the slots 640 in the tube to prevent the plug from spinning as the screw 604 turns. Protrusion 642 may be referred to as a key and slot 640 may be referred to as a keyway. The first end 605 of the inner tube 602 features several slots 640 that allow the tube to expand as the tapered inner plug 611 is drawn into it by rotation of the screw 604. Screw 604 may be turned until inner tubular member 602 has expanded sufficiently to cause first end 605 of inner tubular member 602 to fit tightly within outer tubular member 600, and lock its position relative to outer tubular member 600. The screw head 634 protrudes from the small tube plug 610 and is therefore readily accessible yet largely out of the way.

It is appreciated that other locking assemblies known in the art may be used to clamp the tubular portions together and fix the length of a rod assembly. In an embodiment, a two piece compression lock may be used to fix the length of a rod assembly. The outer tubular element may be rotated about the inner tubular element to compress about the inner tubular element and lock the length of the rod assembly. In another embodiment, a wedge member may be substituted for inner plug 611 to expand inner tubular element 602 within outer tubular element 604 and lock the tubular elements together. In another embodiment, hydraulic expansion may be used to lock the tubular elements together at a desired length. In another embodiment, a dovetail and tab system may be used to lock the tubular elements together at a desired length. In another embodiment, a ball and ramp frictional lock may be used to lock the tubular elements together.

Figure 11:
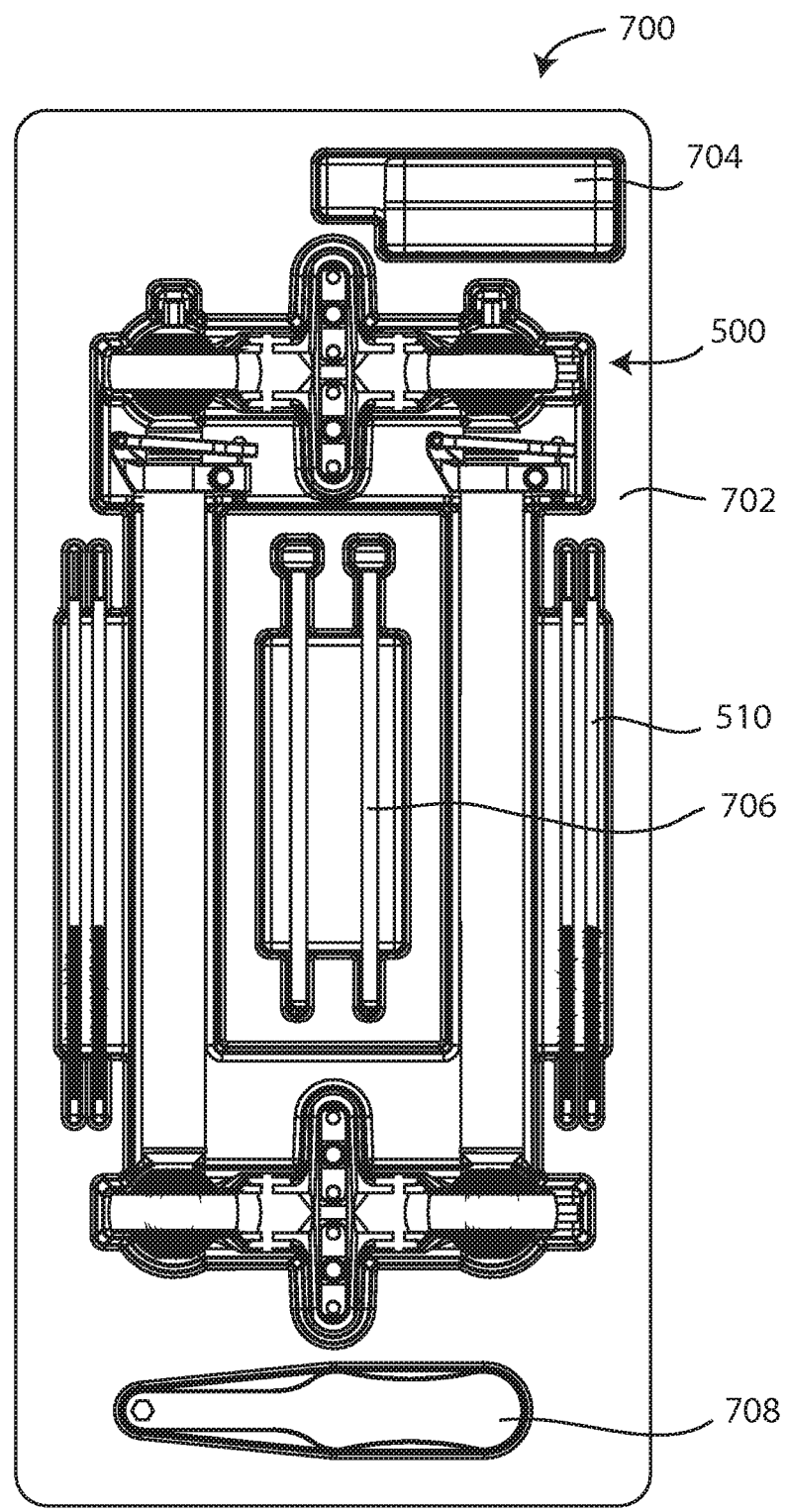
FIG. 11 is a top-down view of a kit including a tray, the external fixation system of FIG. 1, a plurality of bone pins, a drill guide, drill sleeves, and a wrench.

In an embodiment, external fixation system 500 is available in a kit 700, as shown in FIG. 11. Kit 700 may include a tray 702, the pre-assembled external fixation system 500, a plurality of bone pins 510, 560 and/or 562, a drill guide 704, drill sleeves 706, and/or a wrench 708. The kit may be sterile packaged in the peel-pack tray 702, which may be sealed.

In a method of use, kit 700 is opened and the drill guide 704 removed. The drill guide 704 is positioned at a first bone portion on the patient, drill sleeves 706 are inserted into the drill guide, and passages are drilled through drill sleeves and guide, through the adjacent tissues, and into the bone portion. The drill sleeves may prevent soft tissue from wrapping around the drill and/or pin during this step. One or more of the bone pins 560, 562 are inserted through the drilled passages and fixed in the first bone portion. In an alternative embodiment, the pins may be placed without the use of the drill guide and drill sleeves; in one alternative, the system 500 may be removed from the kit and positioned so that the first and second clamping assemblies 502, 504 are on opposite sides of the fracture, joint, or other discontinuity, and the pins may be placed through the first clamping assembly 502.

The system 500 is removed from the kit and positioned so that the first clamping assembly 502 is placed over the one or more bone pins 560, 562 with each bone pin 560 and/or 562 received in a pin bore 542. The fixation bolts 522, 524 are tightened to fix the clamping body 520 to the bone pin(s). The system 500 may be lengthened or shortened by axially translating outer tubular members 600 relative to the inner tubular members 602. The length of system 500 is adjusted to span the joint and/or fracture. To adjust the system length, the second clamping assembly 504 may be pulled axially toward or away from the first clamping assembly 502 to lengthen or shorten the assembly. When the desired length is achieved, the second clamping assembly 504 may then be used as a drill guide for one or more additional bone pins 560, 562 to be fixed in the second bone portion. The additional bone pin(s) may be placed in the second bone portion out of plane from the bone pin(s) in the first bone portion. After at least one additional bone pin is placed in the second bone portion, the second clamping assembly is mounted on the additional bone pin(s), and the fixation bolts 522, 524 of the second clamping assembly 504 are tightened to fix the second clamping body 520 to the additional bone pin(s) in the second bone portion. It is noted that the polyaxial connections allow the system 500 to twist sufficiently to allow the clamping assemblies 502, 504 mount to first and second sets of bone pins, respectively, which are out of plane from one another. The tab members 670 are removed. The system 500 is lengthened to provide traction, reduce the fracture and establish the proper limb length between the first and second bone portions, the inner tubular elements 602 non-rotatably sliding relative to the outer tube elements 600. The system 500 can be lengthened generally parallel to axis 541, within the polyaxial range of motion, by grasping and pulling clamping assembly 502 axially away from clamping assembly 504. Alternatively, the practitioner may grasp the patient's limb, at the foot for example, and pull axially to lengthen the limb and the system 500. When lengthening ceases, the system 500 automatically provisionally locks in a one-way manner as described above, with binding collars 624 engaged against inner tubular elements 602, in what may be referred to as primary locking. The provisional locking may occur when the clamping assembly 502 is released from the tension of pulling. In this arrangement, the practitioner may apply distraction forces intermittently, and may rely upon the one-way lock to maintain a length-stable construct during periods of no distraction force. This may be advantageous to the practitioner, as rest periods may be taken without sacrificing reduction. The rest periods may also permit reassessment of reduction quality, or they may allow gradual atraumatic stretching of swollen, cramped, or spasming muscles or other soft tissues. The system facilitates obtaining an initial reduction followed by an iterative process of refining the reduction without the stress and fatigue associated with constantly maintaining traction on the limb. For example, the reduction may be refined by rotating one bone portion relative to the other bone portion.

After provisional locking at the desired length, at least one of the screws 626 may be tightened to lock the locking collar 620 around the rod assembly, in what may be referred to as secondary locking by activating a second locking mechanism. The limb or bone portions may be further manipulated to achieve proper segment alignment; the spherical portions 612, 614 may polyaxially rotate within their respective inner clamping surfaces 570, 580. For example, one or both of the bone portions may be rotated while the system 500 automatically maintains the desired length. Once the desired bone alignment is achieved, the clamping bolts 530 on each clamp assembly 502, 504 are tightened to lock the clamping assemblies 502, 504 to the rod assemblies 506, 508 with the clamping surfaces 570, 580 compressing around the spherical portions 612, 614 to prevent further polyaxial motion. Wing nuts 533 may be finger tightened to tighten the clamping bolts 530. The remaining screw 626 may also be tightened at this time, if loose. The locking screws 604 in each rod assembly 506, 508 are tightened to further lock the relative position of the telescoping inner and outer tubular elements 600, 602, in what may be referred to as tertiary locking by activating a third locking mechanism. During the procedure, wrench 708 may be used to adjust the screws and bolts of the assembly 500.

The one-piece assembly 500 and one-way automatic locking of the rod assemblies 506, 508 can be advantageous when quick, secure setting of a patient's limb or joint is desired. In contrast with external fixation systems which require assembly of separate rods, clamps and other structures during the external fixation procedure, system 500 is pre-assembled and packaged as one piece which is easily manipulated in a user's two hands. After mounting to the bone pins, system 500 is easily telescopically lengthened by pulling one clamping assembly 502 away from the other clamping assembly 504; when the clamping assembly is released the automatic one-way locking mechanism prevents collapse or shortening of the assembly 500. The one-way provisional locking mechanism maintains the length of the assembly 500 while final adjustments are made and the secondary locking mechanisms are deployed.

The system 500 provides single point tightening and loosening at each one of the locking mechanisms. Length can be locked progressively, or unlocked and adjusted, without unlocking the clamps, and vice versa.

For ease of use, indicia or labeling may be provided on locking screws or other parts. In one non-limiting example, fixation bolts 522, 524 are each marked with a '1' to indicate that they should be actuated first. Similarly, clamping bolts 530 may be marked with a '2'; screws 626 may be marked with a '3', and locking screws 604 may be marked with a '4' to indicate the proper order of actuation and locking. In other embodiments, locking may occur in a different order and the screws or parts may be labeled accordingly.

The clamping bodies 520, locking collars 622 and binding collars 624 may be injection molded in plastic, preferably in a fiber reinforced material to resist creep under a prolonged load. For example fiber-filled PEEK (polyetheretherketone) may be used, and may incorporate glass or carbon fibers. In another embodiment, the clamping bodies are made from machined aluminum. The pins, bolts, screws, nuts and springs may be made of stainless steel or a stainless alloy, preferably non-magnetic. The fixation plates 526-529 and binding collar 624 may be made of stainless steel or other metal, preferably non-magnetic. The locking collar 622, and inner and outer tubular elements 602, 600 may be formed of aluminum. The spherical portions 612, 614 may be cast, may be machined from aluminum, or may be molded from PEEK. Inner plug 611 may be injection molded in plastic, or in other embodiments may include aluminum or fiber-filled PEEK. Some or all parts may be radiolucent. It is appreciated that system 500 may be provided in various sizes and/or lengths so that a practitioner can select a system suited to the size or needs of the patient. For example, longer or shorter rod assemblies may be used to build systems with longer or shorter overall lengths. Rods of various diameters may also be available to scale the external fixation system to the intended use. It is also appreciated that in an embodiment, only one rod assembly may be included in the system. In another embodiment, more than two rod assemblies may be included in the system, with an appropriate number of clamps for clamping the rod assemblies.

Another embodiment includes an external fixation system 800 which may be referred to as an ankle spanning system 800 or joint spanning system, although external fixation system 800 may also be used to span a fracture, osteotomy, epiphyseal plate, or other discontinuity between hone portions. Referring to FIGS. 12-18B, external fixation system 800 includes the first clamping assembly 502, the first rod assembly 506 and the second rod assembly 508, and a clamping subassembly 802.

The clamping subassembly 802, which may be referred to as an ankle clamping subassembly, can connect to and extend between the first and second rod assemblies 506, 508, and includes a first clamping strut assembly 804, a second clamping strut assembly 806, a spanning member 808, and a pin clamp assembly 810. Two calcaneal pins 812, 814 extend between the first and second clamping strut assemblies 804, 806; each calcaneal pin includes a threaded portion 815. The first clamping assembly 502, first rod assembly 506 and second rod assembly 508 are as described above with reference to FIGS. 1-10; in this embodiment the rod assemblies may be shorter than those depicted in FIGS. 1-10. The external fixation system 800 can provide rigid fixation of the ankle joint, to stabilize the foot and ankle with respect to the tibia, for example in the case of a lower tibial fracture or an injured ankle joint.

Figure 14:
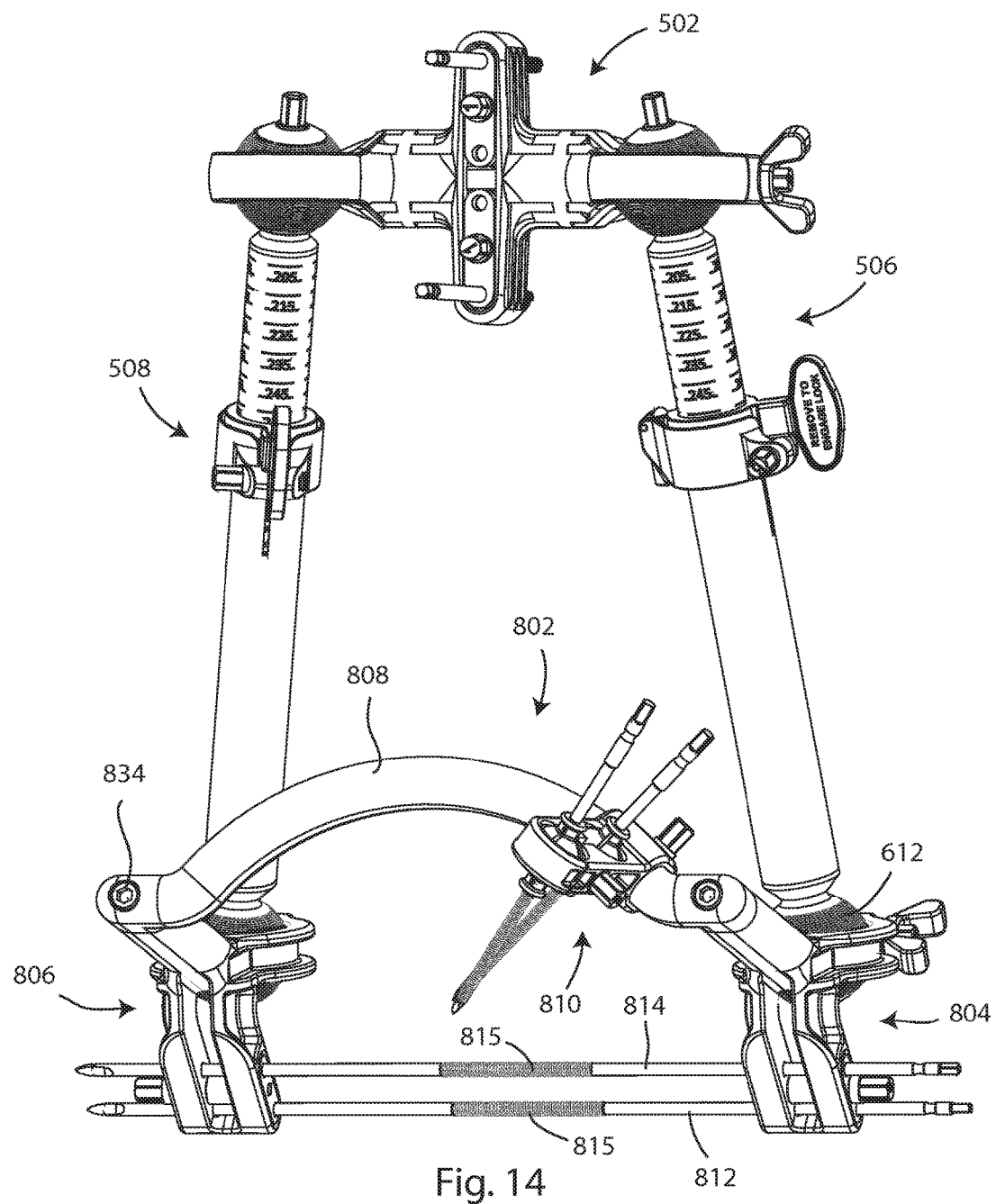
FIG. 14 is a perspective view of the external fixation system of FIG. 12.
Figure 15A:
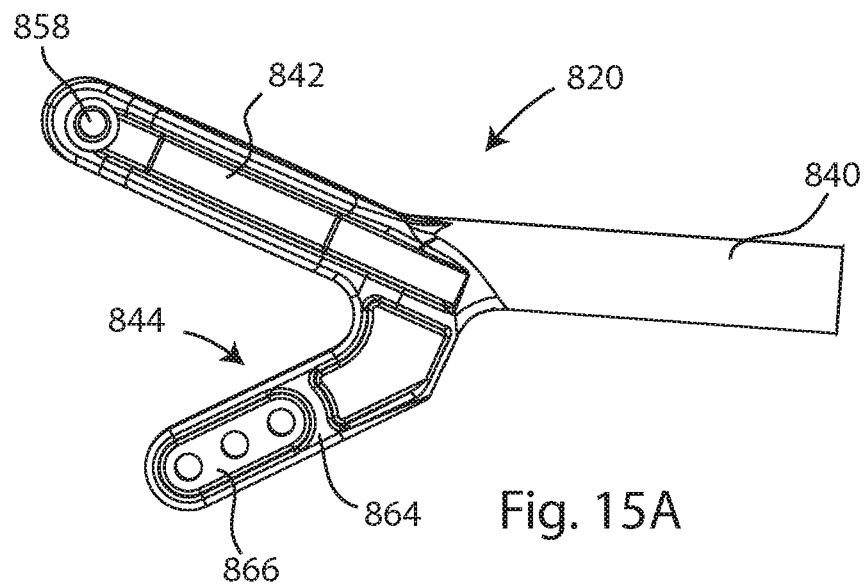
FIG. 15A is a side view of a clamping strut of the external fixation system of FIG. 12.
Figure 15B:
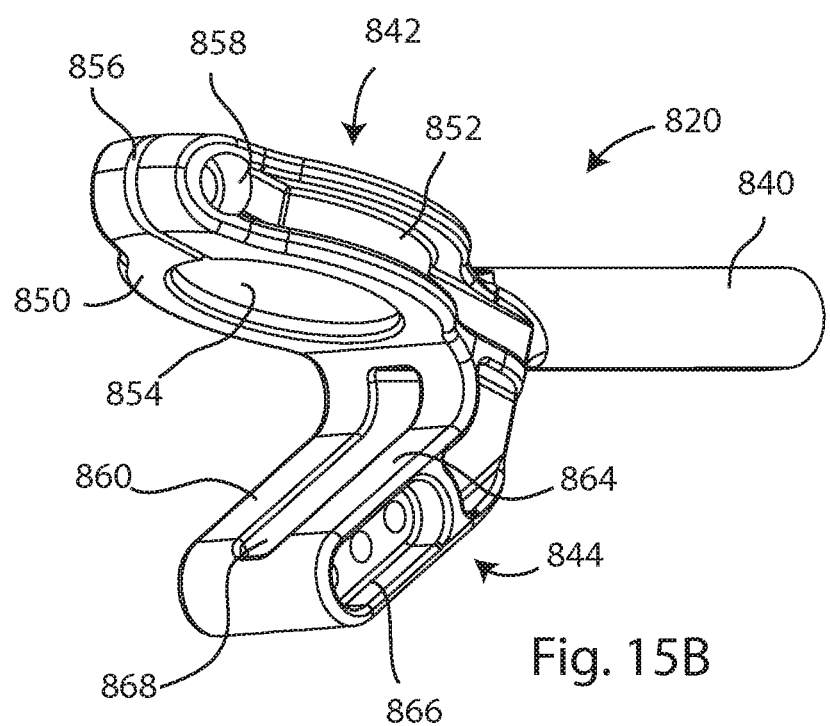
FIG. 15B is a posterior perspective view of the clamping strut of FIG. 15A.
Figure 16:
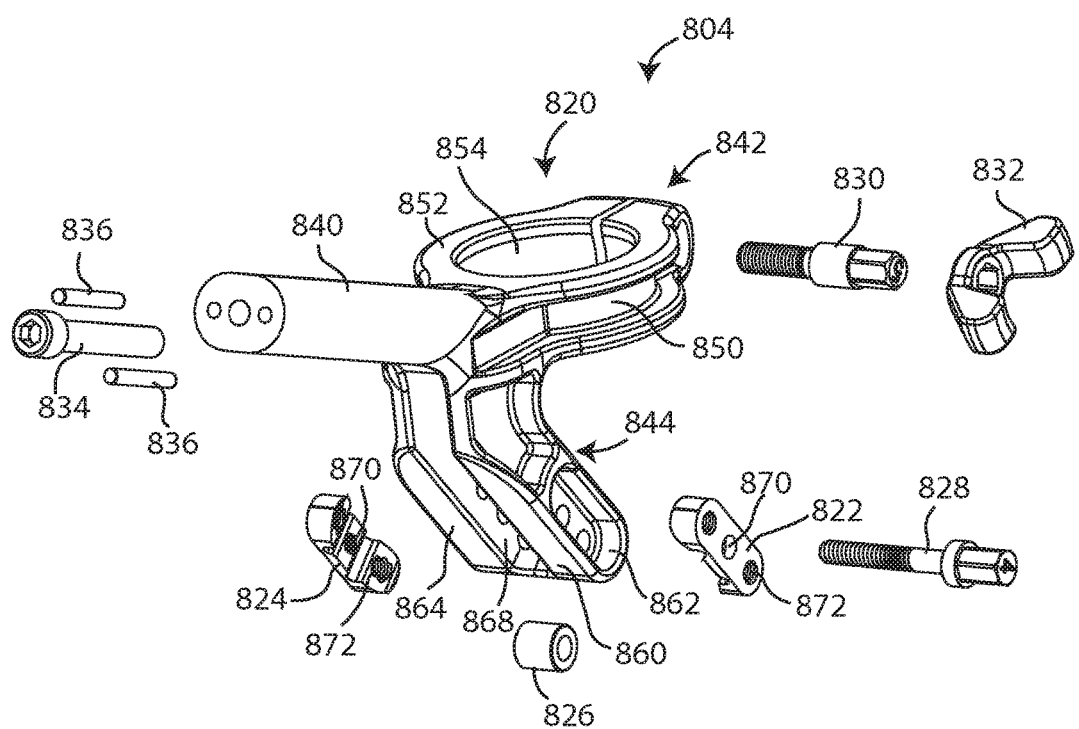
FIG. 16 is an exploded anterior perspective view of a clamping strut assembly of the system of FIG. 12.

Referring to FIGS. 14-16, the first and second clamping strut assemblies 804, 806 may be mirror images, or may be identical to one another except for the direction in which locking bolts, screws, or pins are inserted; thus the description of first clamping strut assembly 804 also applies to assembly 806. First clamping strut assembly 804 includes a clamping strut 820, first and second fixation plates 822, 824, spacing member 826, first fixation bolt 828, second fixation bolt 830, nut 832, a fixation member 834 and two dowel pins 836. The clamping strut 820 includes a strut portion 840, a split clamp portion 842, and a pin clamp portion 844. From a side view, the clamping strut may be generally Y-shaped. The strut portion 840 may be straight, and oval in cross section, although other cross-section shapes such as circular, square or rectangular are contemplated within the scope of the disclosure. The strut portion 840 includes a fixation member bore 841 and may include additional bores to receive dowel pins, to enable connection to the spanning member 808. At least one of the bores in the strut portion may be threaded. In an embodiment, fixation plates 822, 824 are structurally the same as fixation plates 526-529. Each fixation plate 822, 824 includes a bolt opening 870 and several pin openings 872. Bolt and pin openings 870, 872 may be threaded or non-threaded. It is noted that the threaded portion 815 on each calcaneal pin may be smaller diameter than threading in the pin openings 872 on the fixation plates, allowing the calcaneal pins to be freely inserted through the fixation plates.

The split clamp portion 842 of the clamping strut 820 includes first and second clamp arms 850, 852 which face one another and encircle a spherical clamping surface 854, which is interrupted by a gap 856. A fixation bore 858 extends through a distal end of the split clamp portion 842, and is interrupted by the gap 856. When operatively assembled as in FIG. 14, the spherical portion 612 of rod assembly 506 is received within the clamp arms 850, 852 and encircled by the spherical clamping surface 854 so that the spherical portion 612 is captive within the clamp arms 850, 852. The rod assembly 506 may be polyaxially adjustable within the split clamp portion 842 until a desired position is reached. Second fixation bolt 830 may be actuated to draw the first and second clamp arms 850, 852 together, closing the gap 856 and locking the position of the rod assembly 506 relative to the clamping strut 820.

The pin clamp portion 844 includes a first support arm 860 having a first recess 862, opposite a second support arm 864 having a second recess 866, each recess shaped to receive a fixation plate 822, 824. The support arms 860, 864 are separated by an arm gap 868. When operatively assembled as in FIG. 14, the first fixation plate 822 is received in first recess 862, second fixation plate 824 is received in second recess 866, and spacing member 826 is received between the support arms 860, 864 in the arm gap 868. First fixation bolt 828 extends through bolt opening 870 the first fixation plate 822, through the spacer member 826 and into the bolt opening 870 in second fixation plate 824. Calcaneal pins 812, 814 extend transversely through pin openings 872 in the fixation plates, through the support arms 860, 864, and through the arm gap 868. When fixation bolt 828 is tightened, threads on the fixation bolt 828 may engage threads in the bolt opening 870 on the second fixation plate 824 so that tightening the bolt draws the first and second fixation plates toward one another and one or both of fixation plates 822, 824 may be deformed. The pin openings 872 frictionally bind against calcaneal pins 812, 814 preventing them from further axial translation relative to the clamping strut assembly 804. It is appreciated that in other embodiments, other methods of pin capture or fixation known in the art may be used.

Figure 17A:
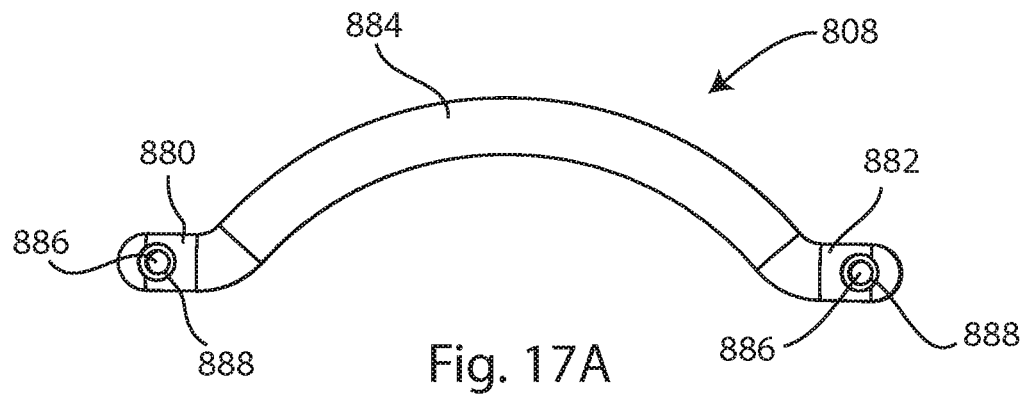
FIG. 17A is an anterior view of the spanning member of the system of FIG. 12.
Figure 17B:
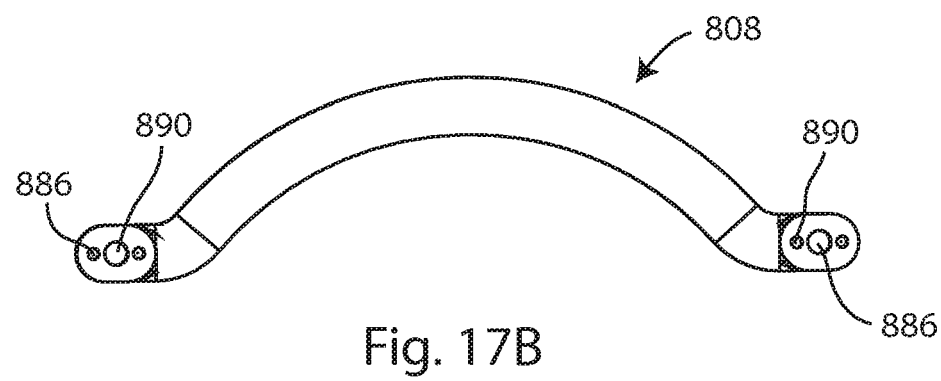
FIG. 17B is a posterior view of the spanning member.
Figure 17C:
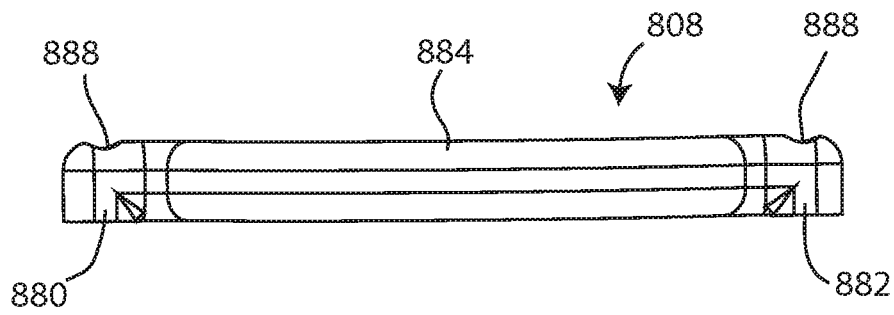
FIG. 17C is a superior view of the spanning member.

Referring to FIGS. 17A-17C, spanning member 808 includes first and second attachment sections 880, 882 which are bridged by a span section 884. In the embodiment shown span section 884 is curved to fit over a patient's appendage. The size, shape and curvature of the spanning member 808 may be varied to accommodate variations in patient size or appendage configuration; in some embodiments the spanning member may be straight. Each attachment section includes a first bore 886 and one or more secondary bores 890. On an outer side of the member 880, a recess 888 surrounds the first bore 886. As seen in FIGS. 14 and 16, spanning member 808 may be operatively attached to each clamping strut assembly 804, 806. Dowel pins 836 are received in openings on the clamping struts 820 and in the secondary bores 890 in the spanning member. Fixation member 834 extends through first bore 886 and into bore 841 on the clamping strut 820 to secure the spanning member 808 to the clamping strut 820. A head portion of the fixation member 834 is received in the recess 888 to provide a low profile to the assembly.

It is appreciated that variations in the configuration of the clamping strut assemblies 804, 806 and the spanning member 808 may occur. For example, in another embodiment the strut portions may be shorter than those depicted, and the attachment sections 880, 882 may extend toward the strut portions. In another embodiment, a separate spanning member may not be present; instead the spanning member may be integrally formed with the clamping strut assemblies to bridge between them. In another embodiment, the spanning member may be absent; the calcaneal pins may form the connection between the clamping strut assemblies.

Figure 18A:
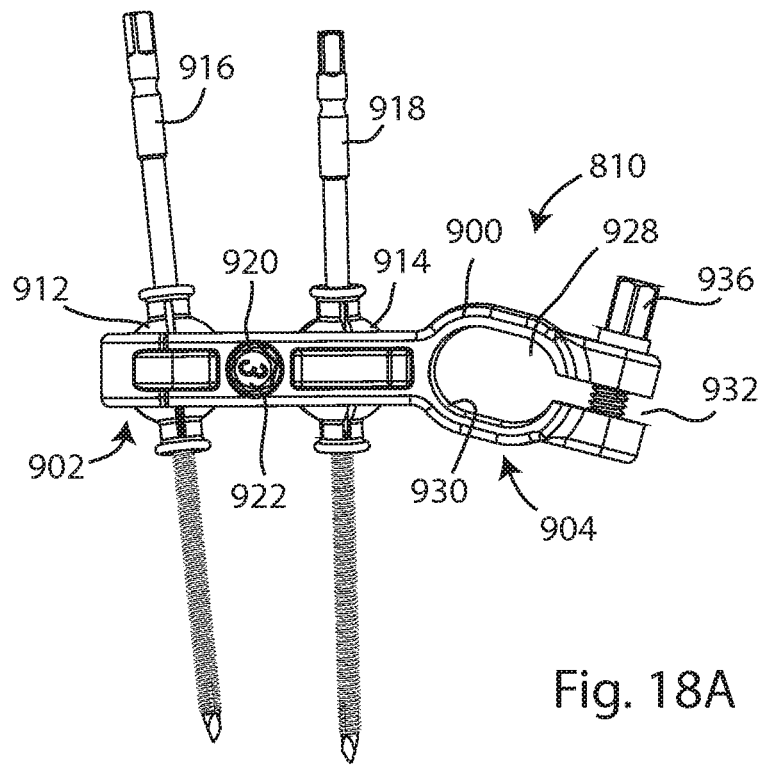
FIG. 18A is a side view of the pin clamp assembly of FIG. 12.
Figure 18B:
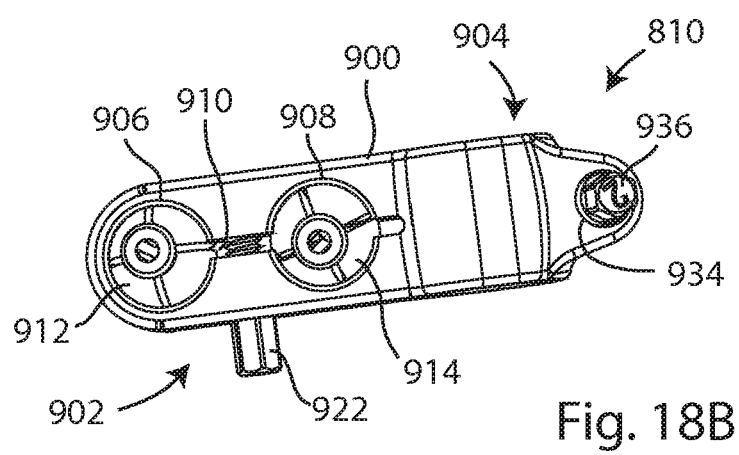
FIG. 18B is a top view of the pin clamp assembly.

Referring to FIGS. 18A and 18B, pin clamp assembly 810 includes a clamp body 900 having a pin clamp portion 902 and a spanning member clamp portion 904. The clamp portions 902, 904 may be angled relative to one another. The pin clamp portion 902 includes first and second spherical openings 906, 908. A slot 910 intersects both spherical openings. A first split sphere 912 is received in the first spherical opening 906 and a second split sphere 914 is received in the second spherical opening 908. A first fixation pin 916 is received through the first split sphere 912 and a second fixation pin 918 is received in the second split sphere 914. The split spheres are polyaxially adjustable within the spherical openings, allowing the trajectories of fixation pins to be adjusted to connect with targeted bone portions, such as a metatarsal bone, or other structures. A first bolt opening 920 extends through the pin clamp portion 902 transverse to the spherical openings, and receives a first clamping bolt 922. When clamping bolt 922 is tightened, the width of slot 910 decreases and the spherical openings 906, 908 are compressed around the spherical members 912, 914, locking the positions of the spherical members and the captured pins 916, 918.

Spanning member clamp portion 904 includes a member opening 928 surrounded by a member clamping surface 930. Both the member opening 928 and clamping surface 930 are interrupted by a member clamping gap 932. A second bolt opening 934 extends through clamp portion 904 and a second clamping bolt 936 extends through the bolt opening 934, bridging the gap 932. When operatively assembled as in FIG. 12, for example, spanning member 808 is received in the member opening 928, and the pin clamp assembly 810 may be translated along the spanning member 808 until a desired or targeted position is reached. Second clamping bolt 936 is actuated to close the gap 932 and compress clamping surface 930 around the spanning member 808, preventing any further translation of the pin clamp assembly 810 relative to the spanning member 808.

In an embodiment, external fixation system 800 is available in a kit. The kit may include a tray, the pre-assembled external fixation system 800, a plurality of bone pins 560, 562, 916, 918, calcaneal pins 812, 814, a drill guide 704, drill sleeves 706, and/or a wrench 708. The kit may be sterile packaged in the tray.

Figure 12:
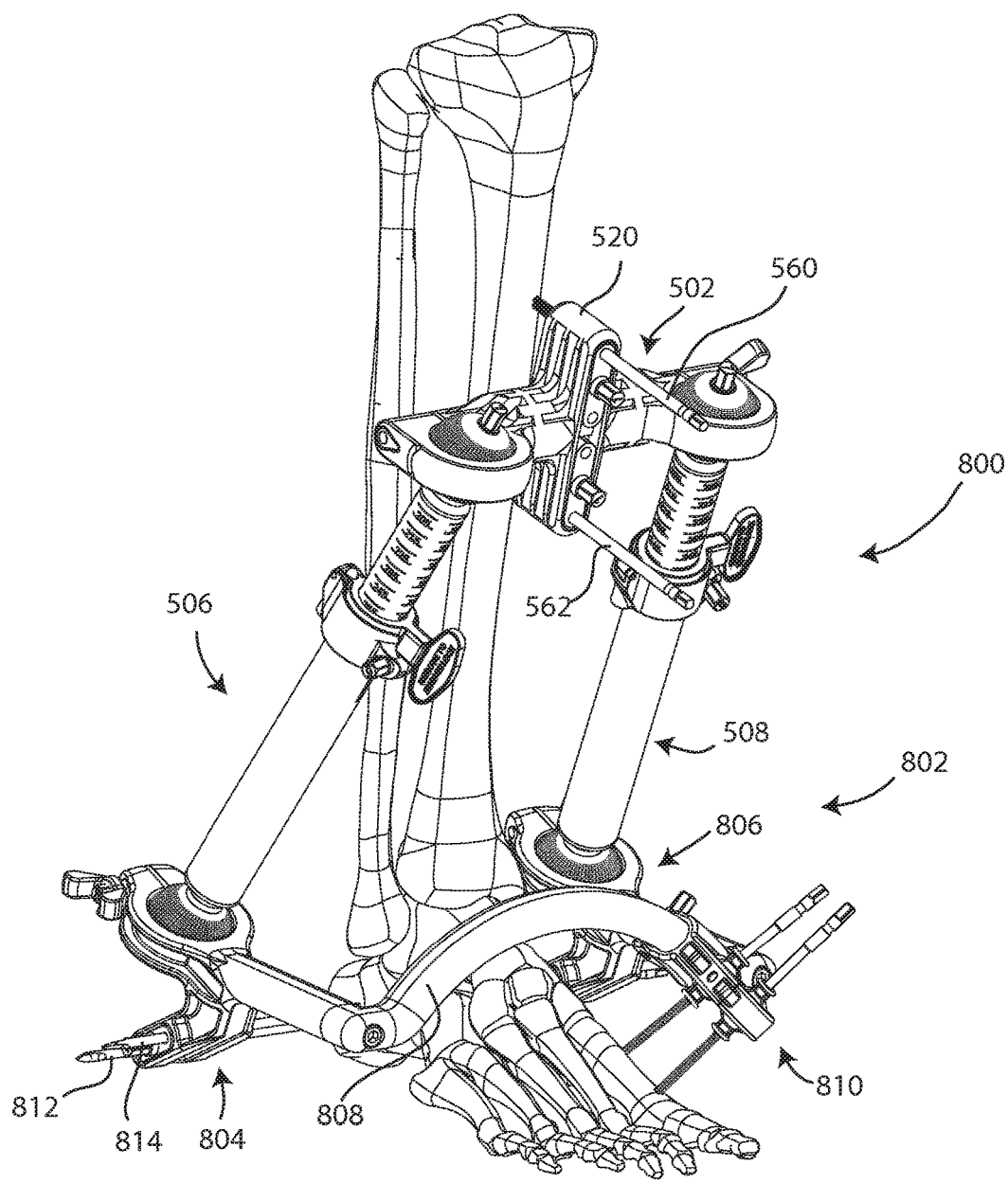
FIG. 12 is a perspective view of another external fixation system, secured to a tibia, a calcaneus, and a metatarsal to span an ankle joint, the system including a clamping assembly, two rod assemblies, two clamping strut assemblies, a pin clamp assembly, a spanning member and a plurality of bone and calcaneal pins.
Figure 13:
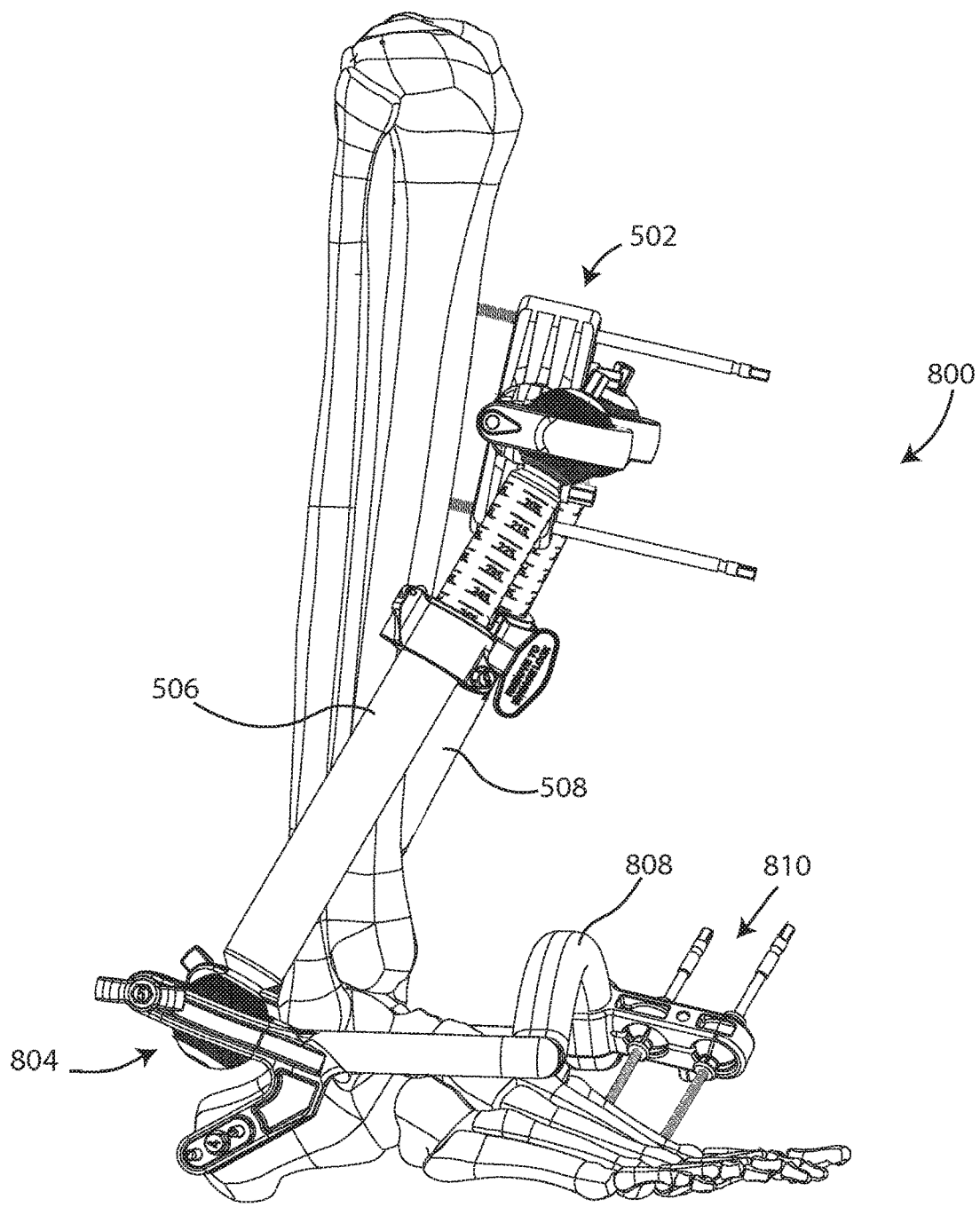
FIG. 13 is a side view of the external fixation system of FIG. 12 secured to the tibia, calcaneus, and metatarsal.

In a method of use of system 800 to immobilize an ankle joint, one or more of the following steps may be present. The tray is opened and the system 800 is removed from the tray. With reference to FIG. 12, the first bone pin 560 is placed in the tibia. The pre-assembled system 800 with clamping assembly 502 is placed over the first bone pin 560, with pin 560 extending through a pin opening 542 in clamp body 520. The spanning member 808 is rested over the foot, with the first and second clamping strut assemblies 804, 806 along either side of the foot in a generally aligned position. Using the clamping assembly 502 as a guide, the second tibial pin is extended through another pin opening 542 in clamp body 520 and into the tibia. The clamping assembly 502 is locked to the bone pins 560, 562 by tightening fixation bolts 522, 524. The first and second clamping strut assemblies 804, 806 are aligned to the calcaneus and one of the first or second calcaneal pins 812, 814 is driven through first and second clamping strut assemblies 804, 806 as well as the bone. The polyaxial alignment of the rod assemblies 506, 508 is adjusted relative to the clamping assemblies 502, 804 and 806. The polyaxial clamps are provisionally locked by tightening clamping bolt 530 in clamping assembly 502, and by tightening fixation bolts 830 in clamping strut assemblies 804, 806. The pin clamp assembly 89 is slid along the spanning member 808 until it provides the proper approach angle to the great toe metatarsal. The position of the pin clamp assembly 810 on the spanning member is locked by tightening clamping bolt 936 in the spanning member clamp portion 904. One or both metatarsal pins 916, 918 are placed through the polyaxial split spheres 912, 914 and into the metatarsal. The pins 916, 918 are locked into the pin clamp portion 902 by tightening clamping bolt 922.

The other of the first and second calcaneal pins 812, 814 is inserted through the first and second clamping strut assemblies 804, 806 as well as the bone. The calcaneal pins 812, 814 are locked into the first and second clamping strut assemblies 804, 806 by tightening fixation bolts 828 to frictionally lock the pins to the clamping struts 820. The tab members 670 are removed from the rod assemblies 506, 508. If required, the limb is placed in traction to re-establish the proper limb length. When the traction is released, the one-way provisional locking of the rod assemblies as described previously will maintain the established length. Binding collar 624 engages against inner tube 602 to prevent telescopic collapsing, or a decrease in the length of the rod assembly. The limb position may be adjusted as necessary, which may include loosening polyaxial clamping bolts 530, 830, adjusting the relative position of the rod assemblies and re-tightening the polyaxial clamping bolts 530, 830. Screws 626 on locking collars 620 are tightened to prevent axial translation of the inner and outer tubes 602, 600 relative to one another. Locking screws 604 are tightened to expand each inner tube member 602 and lock its position relative to outer tube member 600.

Figure 19:
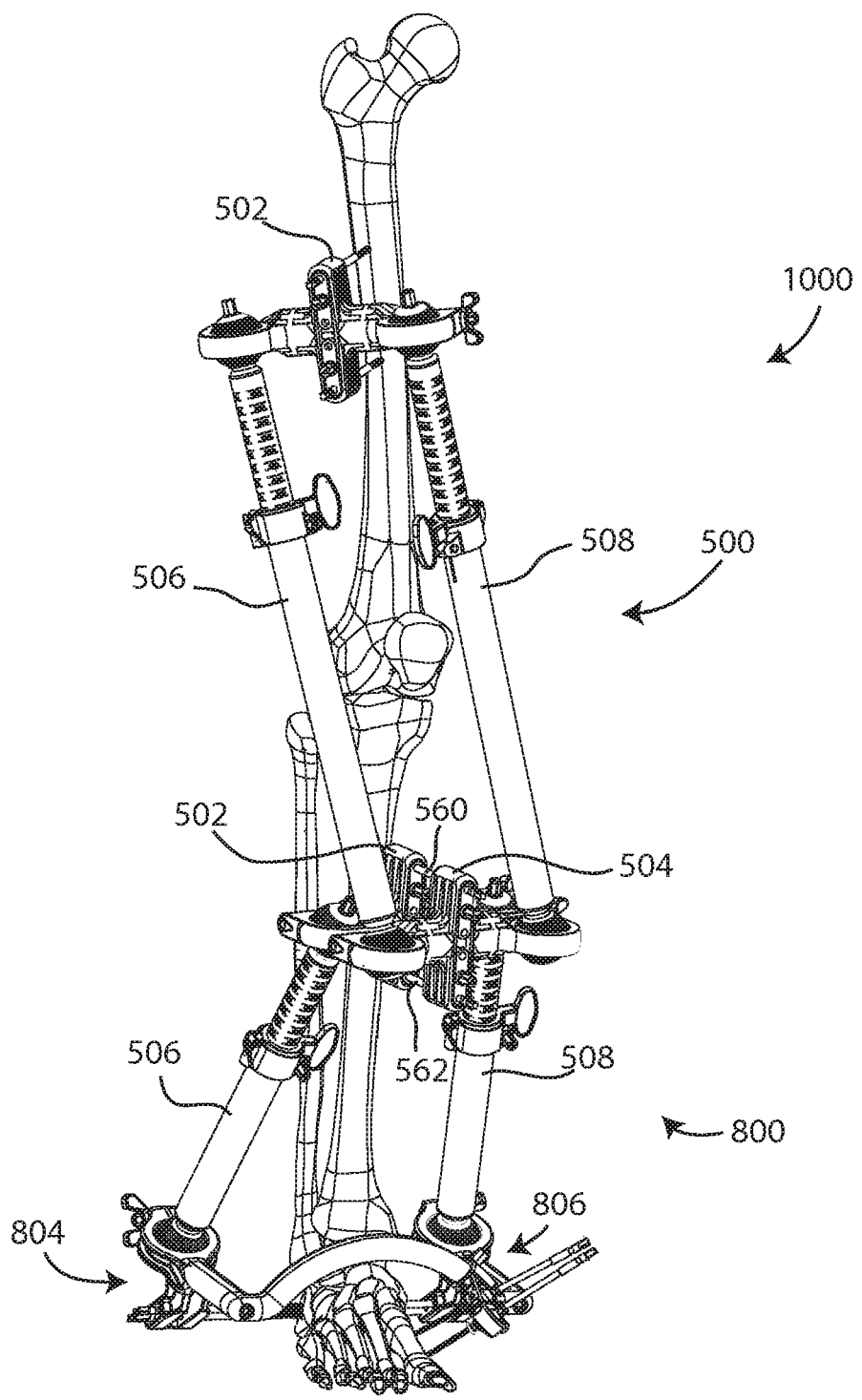
FIG. 19 is an anterior perspective view of a two-level external fixation system mounted to span a knee joint and an ankle joint, the system including the knee spanning external fixation system of FIG. 1 and the ankle spanning external fixation system of FIG. 12 in a stacked configuration, mounted on a common set of tibial bone pins.
Figure 20:
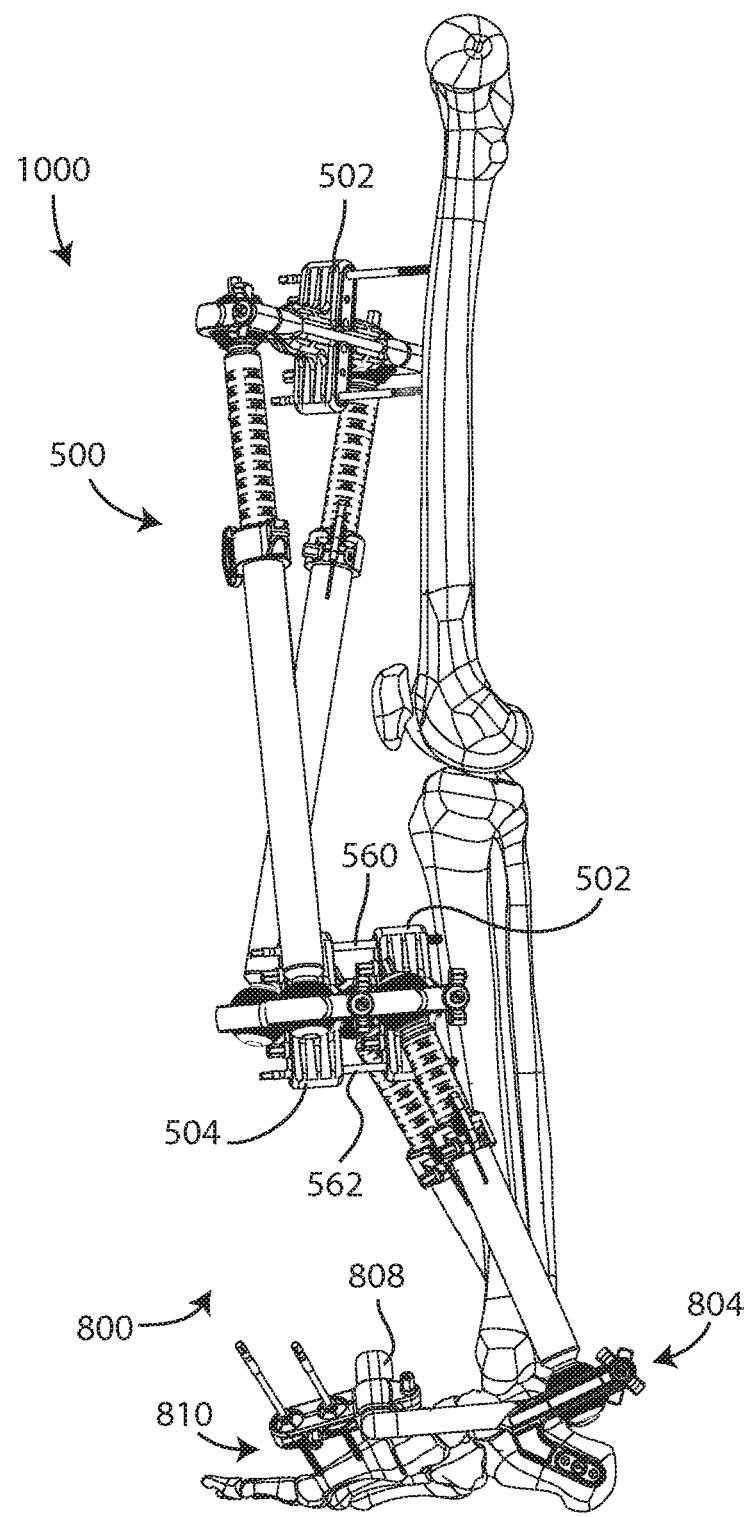
FIG. 20 is a side view of the two-level external fixation system of FIG. 19.

Referring to FIGS. 19 and 20, an external fixation system 1000 is a two-level system which includes system 500, which may span a knee joint, and system 800, which may span an ankle joint. Both systems 500, 800 are mounted on a common set of bone pins 560, 562 which may be mounted in a tibia. System 1000 may provide rigid fixation of the both the knee and ankle joints. Systems 500 and 800 may be vertically stacked on one set of pins without further modification as shown in FIGS. 19 and 20. In another embodiment, the clamp bodies 520 may be modified to allow systems 500 and 800 to be mounted horizontally relative to one another, for example adjacent to one another along second axis 535.

In a method of use of external fixation system 1000, bone pin 560 is mounted in a tibia. External fixation system 800 is mounted on bone pin 560 and as described previously, through the step of the one-way provisionally locking of the rod assemblies. After external fixation system 800 is mounted and provisionally locked, external fixation system 500 is mounted on to bone pins 560, 562 and the rod assemblies are provisionally locked as described previously for system 500. After the provisional locking of systems 500 and 800, final limb adjustments and locking steps for both systems can be iteratively carried out as needed. It will be appreciated that additional systems 500 and/or 800 may be mounted sequentially to extend the zone of fixation as far as necessary.

Another embodiment includes an external fixation system 1100 which may be referred to as a wrist spanning system 1100 or joint spanning system, although external fixation system 1100 may also be used to span a fracture, osteotomy, epiphyseal plate, or other discontinuity between bone portions. Referring to FIGS. 21-27, external fixation system 1100 includes a first clamping assembly 1102, a second clamping assembly 1104, and the first rod assembly 506. The rod assembly 506 extends between and connects the clamping assemblies 1102, 1104 into the single system 1100. The rod assembly 506 may be scaled in length and/or diameter to an appropriate size for the wrist. The clamping assemblies may be referred to as support elements or members, as they support the rod assembly. The first and second clamping assemblies may be mirror images, or may be identical to one another. As described above, using identical assemblies in a system may enable the entire system to be produced more cheaply and/or quickly than a system in which each separate component or assembly is unique.

In use, system 1100 can be secured to the patient in one piece, as a unit. First clamping assembly 1102 may be fixed to a first bone portion by one or more fixation pins 510. Bone screws, bone pins, wires, and/or other fasteners may be used in place of or in combination with fixation pins 510. Second clamping assembly 1104 may be fixed to a second bone portion by additional fixation pin(s) 510. The rod assembly 506, extending between the clamping assemblies, may span a joint or fracture between the first and second bone portions. After the clamping assemblies 1102, 1104 are fixed to the bone portions, the rod assembly 506 may be lengthened or shortened to a desired length and provisionally locked to stabilize the joint or fracture. Following the provisional locking, the polyaxial connections of the assembly may be adjusted, then more permanently locked.

Referring to FIGS. 22-26, clamping assembly 1102 is shown in more detail. Clamping assembly 1104 may be a mirror image, or may be identical to clamping assembly 1102 and will not be described in further detail; the description of clamping assembly 1102 also applies to clamping assembly 1104. Clamping assembly 1102 includes a clamp body 1120 which is formed as a single piece. Clamping assembly 1102 further includes first fixation bolt 1122; first and second fixation plates 1126, 1127; a clamping bolt 1130; first nut 1132; and second nut 1133. The fixation plates may be referred to as locking plates. The rod assembly 506 is polyaxially adjustably connected to the clamping assembly 1102 via a clamp 1134 which is formed as part of the clamping body 1120. Two bone pins 560, 562 extend through the clamping body 1120 to fix the clamping assembly 1102 to a bone portion. In another embodiment, only one bone pin may be used in each clamping assembly.

Referring to FIGS. 21-26, clamp body 1120 may be T-shaped and includes an upper or first surface 1112 and a lower or second surface 1114 opposite the first surface. The clamp body 1120 further includes a first arm 1138 and a second arm 1140 which extend along a first axis 1141, perpendicular to the first clamp 1134, which extends along a second axis 1135. First axis 1141 may be parallel to the longitudinal lengths of rod assembly 506 when the system 1100 is in a neutral or orthogonal arrangement. A bolt opening 1144 extends through the clamping body 1120 in the same direction as the pin openings 1142, 1152 described below. In the example shown, the bolt and pin openings extend in a direction perpendicular to the first axis 1141 and the second axis 1135. A first slot 1148 is recessed into the first surface 1112, and a second slot 1150 is recessed into the second surface 1114, opposite the first slot. The first and second slots are elongated, occupying the majority of the length of the first and second arms 1138, 1140, and the slots are parallel with first axis 1141. A plurality of pin openings or bores 1142 extend through the arms between the first and second slots 1148, 1150, each pin bore sized to receive a bone pin 510. First fixation plate 1126 is housed in the first slot 1148 and second fixation plate 1127 is housed in the second slot 1150. Each fixation plate 1126, 1127 includes at least one plate pin opening 1152, and one of a threaded plate bolt opening 1154 or a non-threaded plate bolt opening 1155. Each fixation plate 1126, 1127 is elongated, having a first extension 1156 and a second extension 1158.

The bone pins 560, 562 are received in pin openings 1142 of clamp body 1120. Each bone pin may pass through a plate pin opening 1152 in a fixation plate, through the first slot 1148, through a pin bore 1142, through the second slot 1150, and out through a plate pin opening 1152 in another fixation plate. The opening for the pins may be non-threaded and/or smooth, to allow the pins 560, 562 to initially be axially translatable relative to the arms 1138, 1140. The translation allows for adjustability of the height of the system 1100 relative to a patient's limb, which may be advantageous if there is tissue swelling, an open wound, and/or a skin abrasion on the limb. It is appreciated that the bone pins may be placed in one or any combination of the pin openings 1142.

Figure 25:
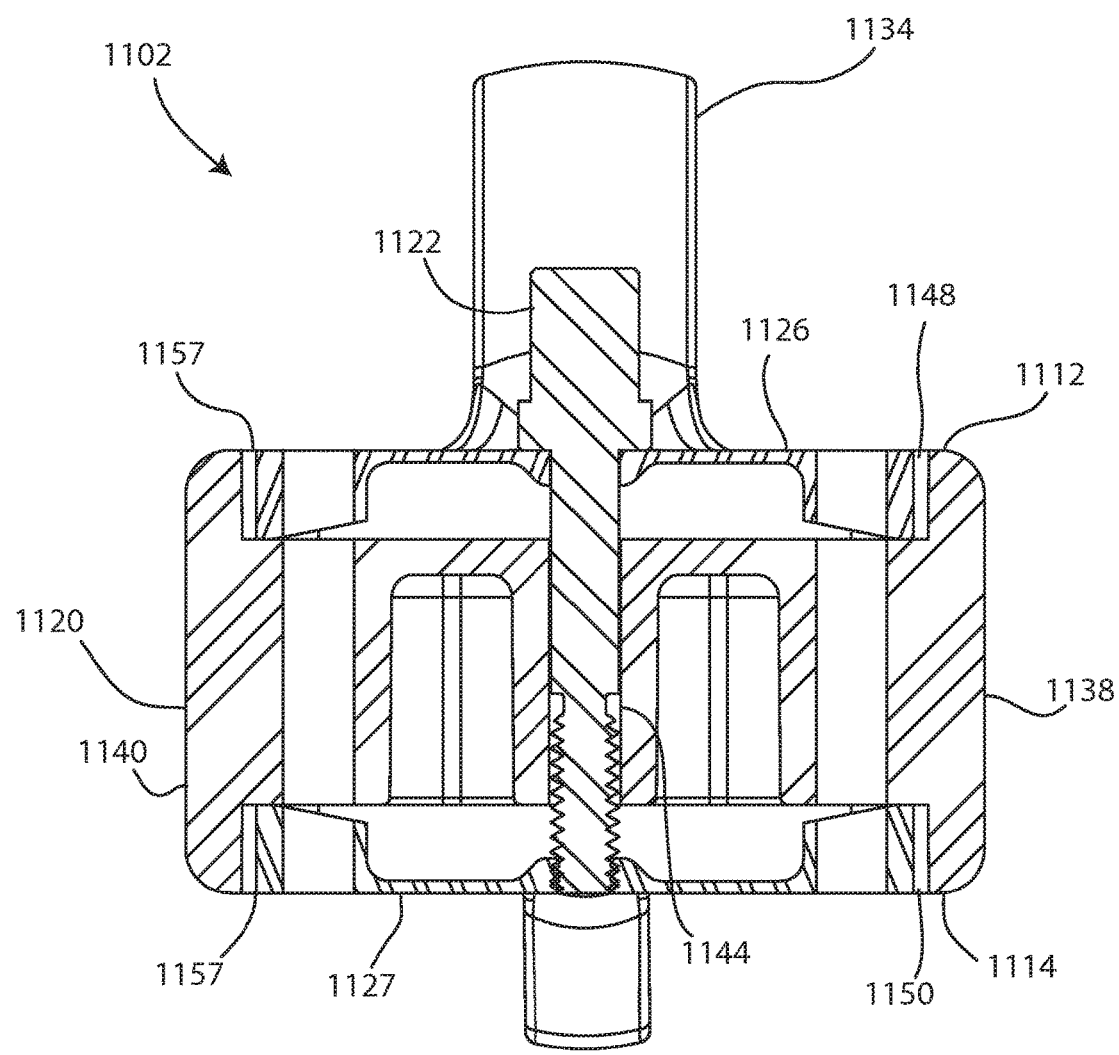
FIG. 25 is a cross-sectional view of the clamping assembly of FIG. 22, comparable to FIG. 5.

Referring to FIG. 25, the first fixation bolt 1122 passes through a non-threaded bolt opening 1155 in first fixation plate 1126, into the first slot 1148, through a bolt opening 1144 and out through second slot 1150 and a threaded plate bolt opening 1154 in second fixation plate 1127. As the threads of bolt 1122 engage threaded plate bolt opening 1154, the center portion of second fixation plate 1127 is drawn toward the center portion of first fixation plate 1126 against the resistance of first and second extensions 1156, 1157 bearing in slots 1148, 1150, causing one or both of fixation plates 1127, 1126 to be elastically or plastically deformed. As a result of the elastic or plastic deformation, the plate pin openings 1152 frictionally bind against pin 562, preventing pin 562 from further axial translation relative to the clamp body 1120. As the plates 1126, 1128 deform, they may bow and decrease in length, which pushes the pin 562 against the side wall of the pin bore 1142. This force creates a secondary locking action relative to the pin 562. It is appreciated that in other embodiments, other methods of pin capture or fixation known in the art may be used.

Figure 21:
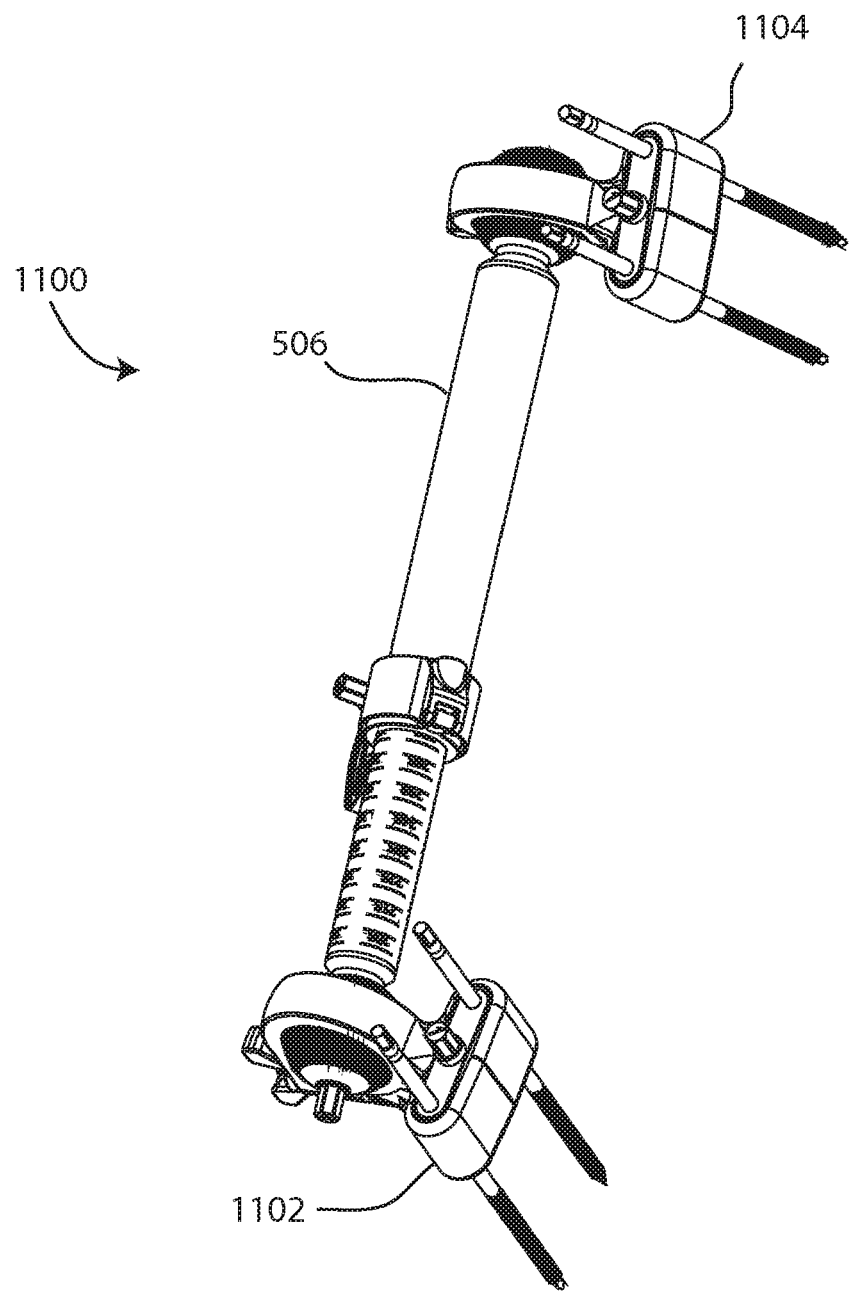
FIG. 21 is a perspective view of yet another external fixation system, the system including two clamping assemblies, a rod assembly, and a plurality of bone pins.
Figure 22:
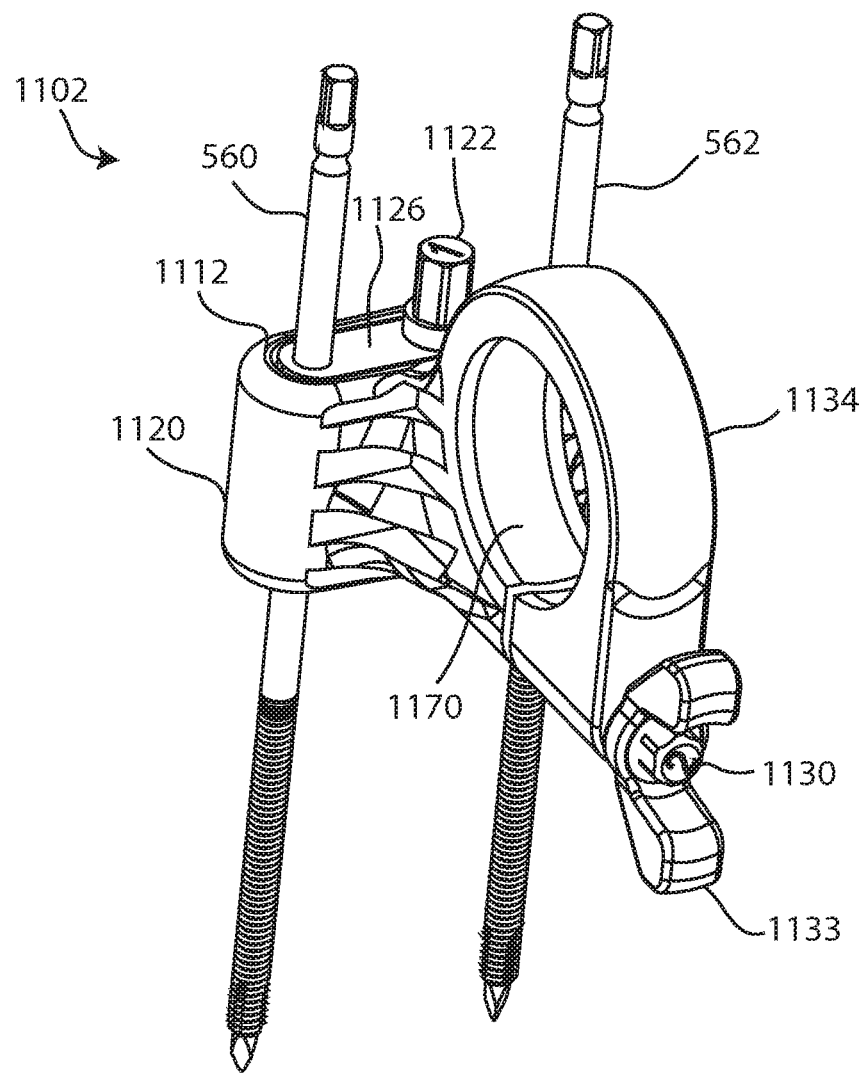
FIG. 22 is a perspective view of a clamping assembly and bone pins of the external fixation system of FIG. 21.
Figure 23:
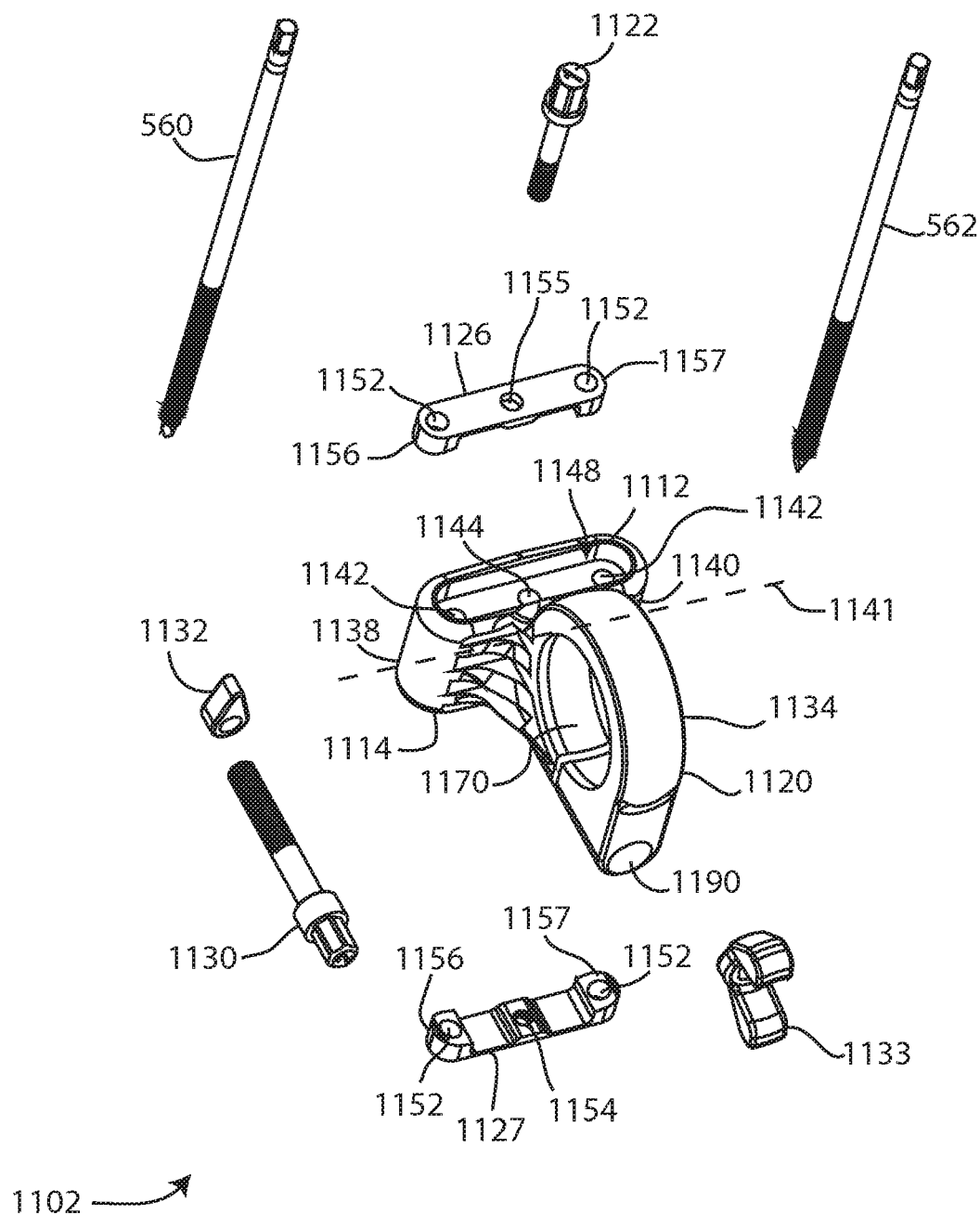
FIG. 23 is an exploded perspective view of the clamping assembly and bone pins of FIG. 22.
Figure 24:
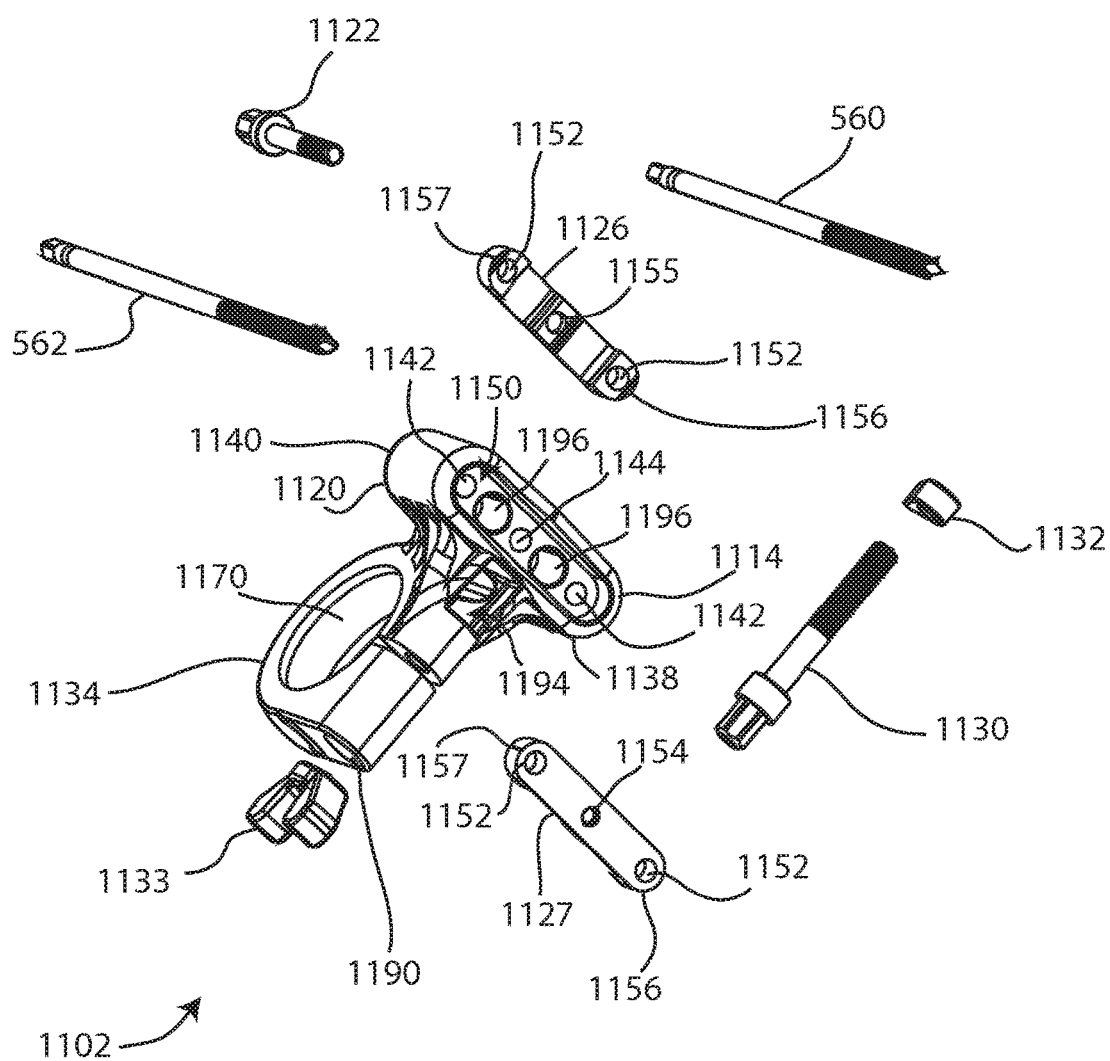
FIG. 24 is another exploded perspective view of the clamping assembly and bone pins of FIG. 22, from a different viewpoint.
Figure 26:
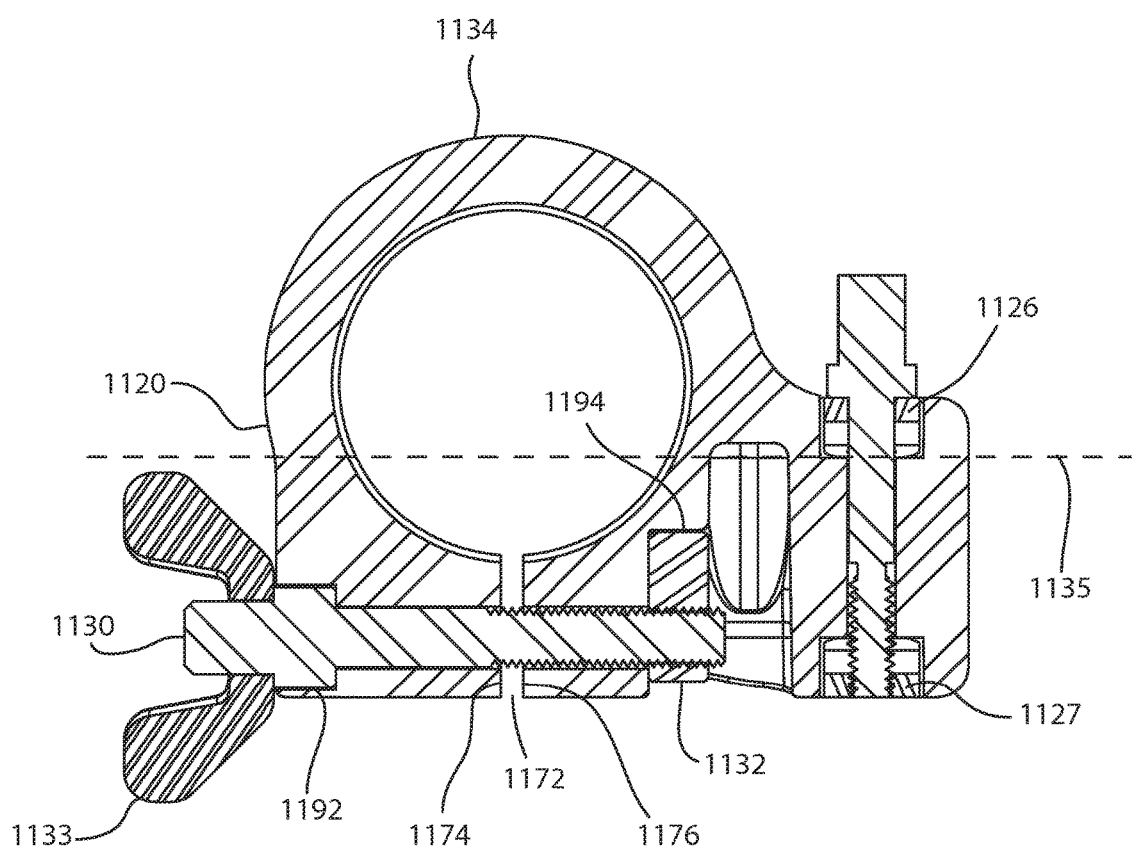
FIG. 26 is another cross-sectional view of the clamping assembly of FIG. 22, comparable to FIG. 6.
Figure 27:
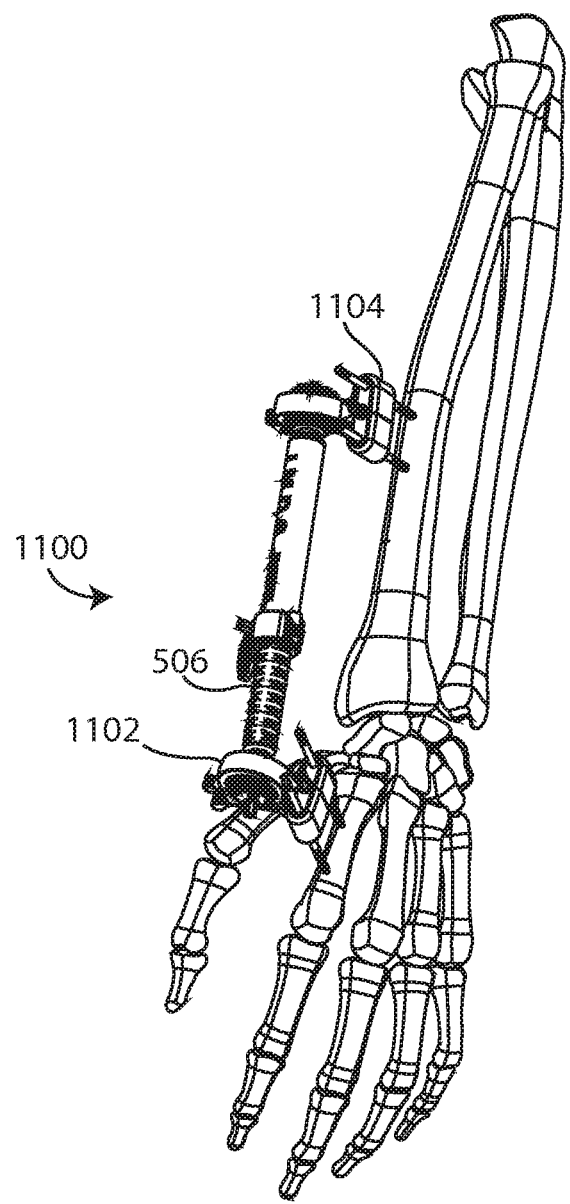
FIG. 27 is a perspective view of the external fixation system of FIG. 21 secured to a radius and a metacarpal to span a wrist joint.

Turning to FIGS. 23-24 and 26, the clamp 1134 is shaped to retain or clamp rod assembly 506 while allowing telescoping movement of the rod assembly to lengthen or shorten the rod assembly. Clamp 1134 has an inner clamping surface 1170 which is spherical in the illustrated embodiment; in other embodiments the clamping surfaces may be partially spherical, conical, cylindrical, flat, polygonal, or another shape. The inner clamping surface 1170 is interrupted by a clamp gap 1172 bounded by opposing first and second clamp surfaces 1174, 1176. In the example shown the inner clamping surface 1170 is smooth, but in an alternative embodiment it may be ridged or roughened. A bore 1190 extends through the clamp 1134, parallel to second axis 1135, intersecting clamp gap 1172. The bore 1190 includes a first recess 1192 at one end and a second recess 1194 at the opposite end. One or more chambers 1196 extend into the clamp body 1120 between the pin openings 1142, and may provide for weight reduction for the clamp body. Clamping bolt 1130 extends through bore 1190 and engages nut 1132. As the clamping bolt 1130 engages the nut 1132, the nut 1132 is captured in second recess 1194. Further actuation of bolt 1130 draws nut 1132 toward the bolt head, engaging recess 1194 and closing gap 1172. Nut 1133, which may be a wing nut, may also be actuated to tighten bolt 1130. As seen in FIG. 21, when rod assembly 506 is assembled with clamp assemblies 1102, 1104 as shown and bolt 1130 is tightened as described, the rod assembly is gripped in the clamps 1134 and prevented from any movement, for example axial, rotation, or polyaxial, relative to the clamp body 1120.

In an embodiment, external fixation system 1100 is available in a kit, similar to that shown in FIG. 11. The kit for external fixation system 1100 may include a tray, the pre-assembled external fixation system 1100, a plurality of bone pins 560 and 562, a drill guide 704, drill sleeves 706, and/or a wrench 708. The kit may be sterile packaged in a peel-pack tray, which may be sealed.

A method of use of external fixation system 1100 may be similar to, or identical to, that described above for external fixation system 500.

The systems disclosed herein may provide advantages over external fixation systems known in the art. For example, providing pre-assembled systems such as 500, 800, or 1100 which are anatomy-specific can reduce the number of parts or inventory necessary to perform an external fixation procedure, compared to systems which are provided as a comprehensive kit of loose parts. Also, having a pre-assembled system can minimize unanticipated disassembly during an external fixation procedure and during tightening and adjustment of the system. The pre-assembled system may therefore provide a low-stress user experience for the practitioner, for example, by eliminating tedious intraoperative assembly or unanticipated disassembly. Use of the pre-assembled systems disclosed herein also reduces or eliminates operating room or procedure time which, for other systems known in the art, is spent assembling a fixation system on the back table. The one-way locking mechanism may retain limb length during tightening and adjustment of the system without requiring constant distraction by the surgeon. The one-way locking mechanism contributes to ease of obtaining fracture reduction, and the provisional locking is secure enough to allow easy adjustment of the reduction while the system is provisionally locked. The removable tab member 670 provides quick conversion between the unlocked configuration and the locked configuration, allowing quick and efficient distraction and reduction. The systems disclosed herein can be applied to a patient by one or two practitioners, which may reduce the number of practitioners needed and overall procedure cost.

In addition to the embodiments shown herein to span the knee, ankle, and/or wrist joints, it is appreciated that principles taught herein may be applied to external fixators and fixation methods for other joints, including but not limited to the elbow, wrist, carpal, tarsal, phalanges, hip, sacrum, shoulder, cranium, and/or intervertebral joints. The technology disclosed herein may also be applied to external fixation and fixation methods for fractures rather than joints.

The apparatus disclosed herein may be made from low cost materials, such as aluminum and/or plastic, using low cost manufacturing techniques such as lathe and mill. In some embodiments, the system may be so inexpensive as to be single-use disposable. In this situation, there would be no re-processing or re-stocking fees charged to the owner of the apparatus.

It should be understood that the present system, kits, apparatuses, and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, a clamping body or assembly described for one system may be used with another system. Features of instrumentation from one example may be applied to instrumentation from another example. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for external fixation of a limb, the limb having a first bone portion and a second bone portion, the method comprising:
   securing a first bone pin to the first bone portion;
   securing a second bone pin to the second bone portion;
   attaching a pre-assembled external fixation system to the first bone pin, the external fixation system comprising: first and second clamp assemblies, first rod assembly, and a one-way locking mechanism; the first rod assembly joined to each of the first and second clamp assemblies, the first and second clamp assemblies at opposite longitudinal ends of the first rod assembly; the first clamp assembly received over the first bone pin;
   attaching the external fixation system to the second bone pin, the second clamp assembly received over the second bone pin;
   and
   activating the one-way locking mechanism to prevent a length of the external fixation system from decreasing, wherein the one-way locking mechanism engages the first rod assembly at a non-discrete location to prevent the length of the external fixation system from decreasing.

2. The method of claim 1, comprising:
   opening a package; and
   removing the pre-assembled external fixation system as a single unit from the package.

3. The method of claim 1, wherein the first rod assembly comprises a removable tab, the method comprising:
   removing the tab to activate the one-way locking mechanism, wherein prior to removal of the tab, the external fixation system is freely adjustable to increase or decrease the length of the external fixation system between the first clamp assembly and the second clamp assembly.

4. The method of claim 1, comprising a second rod assembly, the second rod assembly joined to each of the first and second clamp assemblies.

5. The method of claim 4, wherein the first clamp assembly is identical to the second clamp assembly, and wherein the first rod assembly is identical to the second rod assembly.

6. The method of claim 1, wherein the first rod assembly comprises an inner tubular member received in an outer tubular member, wherein the one-way locking mechanism is a first locking mechanism, wherein the one-way locking mechanism is mounted to the outer tubular member, wherein activating the one-way locking mechanism comprises:
   directly engaging the one-way locking mechanism with the inner tubular member to prevent the inner tubular member from translating relative to the outer tubular member in a first direction.

7. The method of claim 6, wherein the one-way locking mechanism comprises a collar encircling the inner tubular member, wherein the collar frictionally engages with the inner tubular member to prevent the inner tubular member from translating relative to the outer tubular member in the first direction.

8. The method of claim 6, comprising:
activating a second locking mechanism to further prevent the inner tubular member from translating relative to the outer tubular member in the first direction and also in a second direction opposite the first direction.

9. The method of claim 8, wherein the first rod assembly comprises the second locking mechanism, the second locking mechanism comprising a clamp encircling the outer tubular member, the method comprising:
compressing the clamp around the outer tubular member; and
compressing the outer tubular member around the inner tubular member.

10. The method of claim 8, comprising:
activating a third locking mechanism to further prevent the inner tubular member from translating relative to the outer tubular member.

11. The method of claim 10, wherein the first rod assembly comprises the third locking mechanism, the third locking mechanism comprising a plug received in the inner tubular member, the method comprising drawing the plug within the inner tubular member to expand a portion of the inner tubular member.

12. The method of claim 1, comprising:
polyaxially adjusting a position of the first rod assembly relative to the first clamp assembly; and
compressing the first clamp assembly about the first rod assembly to lock the position of the first rod assembly relative to the first clamp assembly.

13. The method of claim 1, comprising:
locking the first clamp assembly to the first bone pin.

14. The method of claim 13, wherein the first clamp assembly houses a first fixation plate and a second fixation plate, wherein locking the first clamp assembly to the first bone pin comprises:
passing the first bone pin through the first and second fixation plates; and
deforming the first and second fixation plates to bind against the first bone pin.

15. The method of claim 1, comprising:
passing a third bone pin into the first clamp assembly; and
securing the third bone pin to the limb.

16. A method for external fixation of a limb, the limb having a first bone portion and a second bone portion, the method comprising:
securing a first bone pin to the first bone portion;
securing a second bone pin to the second bone portion;
attaching a pre-assembled external fixation system to the first bone pin, the external fixation system comprising: first and second clamp assemblies, a first rod assembly comprising a one-way locking mechanism; the first rod assembly joined to each of the first and second clamp assemblies, the first and second clamp assemblies at opposite longitudinal ends of the first rod assembly; the first clamp assembly received over the first bone pin;
attaching the external fixation system to the second bone pin, the second clamp assembly received over the second bone pin; and
activating the one-way locking mechanism, wherein prior to activating the one-way locking mechanism the external fixation system is freely adjustable to increase or decrease a length of the external fixation system between the first clamp assembly and the second clamp assembly, wherein activating the one-way locking mechanism prevents the length of the external fixation system from decreasing, and wherein the one-way locking mechanism engages the first rod assembly at a non-discrete location to prevent the length of the external fixation system from decreasing.

17. The method of claim 16, comprising a second rod assembly, the second rod assembly joined to each of the first and second clamp assemblies.

18. The method of claim 17, wherein the first clamp assembly is identical to the second clamp assembly.

19. The method of claim 16, wherein the first rod assembly comprises an inner tubular member received in an outer tubular member, wherein the one-way locking mechanism is mounted to the outer tubular member, and wherein activating the one-way locking mechanism comprises:
engaging the one-way locking mechanism with the inner tubular member to prevent the inner tubular member from translating relative to the outer tubular member in a first direction.

20. A method for external fixation of a limb, the limb having a first bone portion and a second bone portion, the method comprising:
securing a first bone pin to the first bone portion;
securing a second bone pin to the second bone portion;
attaching a pre-assembled external fixation system to the first bone pin, the external fixation system comprising: first and second clamp assemblies, a first rod assembly comprising a one-way locking mechanism and a disengageable tab; the first rod assembly joined to each of the first and second clamp assemblies, the first and second clamp assemblies at opposite longitudinal ends of the first rod assembly; the first clamp assembly received over the first bone pin;
attaching the external fixation system to the second bone pin, the second clamp assembly received over the second bone pin; and
disengaging the disengageable tab to activate the one-way locking mechanism, wherein prior to disengaging the disengageable tab, the external fixation system is freely adjustable to increase or decrease a length of the external fixation system between the first clamp assembly and the second clamp assembly, and wherein disengaging the disengageable tab prevents the length of the external fixation system from decreasing.

* * * * *